United States Patent [19]

Kishimoto

[11] Patent Number: 5,171,840
[45] Date of Patent: Dec. 15, 1992

[54] RECEPTOR PROTEIN FOR HUMAN B CELL STIMULATORY FACTOR-2

[76] Inventor: Tadamitsu Kishimoto, 5-31, Nakanocho, 3-chome, Tondabayashi-shi, Osaka, Japan

[21] Appl. No.: 298,694

[22] Filed: Jan. 19, 1989

[30] Foreign Application Priority Data

Jan. 22, 1988 [JP] Japan ............................. 63-012387
Jan. 25, 1988 [JP] Japan ............................. 63-012599
Aug. 4, 1988 [JP] Japan ............................. 63-194885
Jan. 14, 1989 [JP] Japan ............................. 107461

[51] Int. Cl.$^5$ .................. C07K 3/00; A61K 37/02; C12P 21/06
[52] U.S. Cl. ................................. 530/350; 530/395; 435/69.1
[58] Field of Search ............... 435/69.1; 530/350, 300, 530/395

[56] References Cited

PUBLICATIONS

Maniatis, Fritsch and Sambrook, Molecular Cloning a Laboratory Manual 1982, pp. 188–199 and 213–246.
Science, vol. 241, 12th Aug. 1988, pp. 825–828; K. Yamasaki et al.
Hirano et al.; Summary of Presentation to the 17th Conference of Japan Immunology.
Kishimoto et al.; Studies of B-Cell Growth, Differentiation and Aberrant Control (in Japanese); Mar. 1989.
Proc. Natl. Acad. Sci. U.S.A., vol. 83, pp. 8957–8961, Dec. 1986.
The EMBO Journal, vol. 5, No. 10, pp. 2529–2537, 1986.
Chemical Abstracts, vol. 109, p. 193, (87407d) Nishikawa.
T. Hirano, et al., *Nature*, "Complementary DNA for a novel human interleukin (BSF-2) that induces B lymphocytes to produce immunoglobulin", vol. 324, pp. 73–76, (1986).
T. Kishimoto et al., *Ann. Rev. Immunol.*, "Molecular Regulation of B Lymphocyte Response", vol. 6, pp. 485–512, (1988).
Hirano et al., *Proc. Natl. Acad. Sci. U.S.A.*, "Human B-cell differentiation factor defined by an anti-peptide antibody and its possible role in autoantibody production", vol. 84, pp. 228–231, (1987).
Tetsuya Taga, et al., *J. Exp. Med.*, "Receptors for B Cell Stimulatory Factor 2", vol. 166, pp. 967–981, (1987).
Brian Seed, *Nature*, "An LFA-3 cDNA encodes a phospholipid-linked membrane protein homologous to its receptor CD2", vol. 329, pp. 840–842, (1987).
Joachim Messing, *Methods in Enzymology*, "New M13 Vectors for Cloning", vol. 101, pp. 20–79, (1983).
C. Tyndall, et al., *Nucleic Acids Research*, "A region of the polyoma virus genome between the replication origin and late protein coding sequences is required in cis for both early gene expression and viral DNA replication", vol. 9, No. 23, pp. 6231–6250, (1981).
S. Nakajima-Iijima, *Proc. Natl. Acad. Sci. U.S.A.*, "Molecular structure of the human cytoplasmic B-action gene: Interspecies homology of sequences in the introns", vol. 82, pp. 6133–6137, (1985).
Leland Ellis et al., *Cell*, "Replacement of Insulin Receptor Tyrosine Residues 1162 and 1163 Comprises Insulin-Stimulated Kinase Activity and Uptake of 2--Deoxyglucose", vol. 45, pp. 721–732, (1986).
Michael Wigler, *Cell*, "Biochemical Transfer of Single-Copy Eucaryotic Genes Using Total Cellular DNA as Donar", vol. 14, pp. 725–731, (1978).
Gilbert Chu et al., *Gene*, "SV40 DNA transfection of cells in suspension: analysis of the efficiency of transcription and translation of T-antigen", vol. 13, pp. 197–202, (1981).

*Primary Examiner*—Christine Nucker
*Assistant Examiner*—Hazel F. Sidberry
*Attorney, Agent, or Firm*—Foley & Lardner

[57] ABSTRACT

An isolated receptor protein for human B cell stimulatory factor-2, capable of specifically binding to the human B cell stimulatory factor-2; DNA coding for the above-mentioned receptor protein; expression vectors containing the above-mentioned DNA; host organisms transformed with the above-mentioned expression vector; a process for production of the receptor protein comprising culturing the host organisms in a medium to produce the receptor protein and recovering the receptor protein from the culture; and a antibody reacting with the protein.

6 Claims, 25 Drawing Sheets

Fig. 3-1

(5'-Terminal) TCATGTGCGAGTGGGAAGTCGCACTGACACTGAGCCGGGCCAGAGGGAGAGGAGCCGAGC
GCGGGCGGCGGCCGAGGGACTCGCAGTGTGTGTAGAGAGCCGGGCTGCCCCGGGGCCTGAGCCCGCCCGCCC
ACCGCCCCGCCCCCGCCCCTGCCACCCCTGCCCCCGGTTCCCATTAGCCTGTCCGCCCCTCTGCGCCCATGACTGACTGTAGCCGAGGAGGAAGC (N-Terminal)
Met Leu Ala Val Gly Cys Ala Leu Leu Leu Ala Ala Leu Leu Ala Ala Pro Gly Ala Ala Leu Ala Pro Arg
ATG CTG GCC GTC GGC TGC GCG CTG CTG CTG GCT GCT CTG CTG GCC GCG CCC GGA GCG GCG CTG GCC CCA AGG Arg Cys Pro Ala Gln Glu Val Ala Arg Gly Val Leu Thr Ser Leu Pro Gly Asp Ser Val Thr Leu Thr
CGC TGC CCT GCG CAG GAG GTG GCA AGA GGC GTG CTG ACC AGT CTG CCA GGA GAC AGC GTG ACT CTG ACC Cys Pro Gly Val Glu Pro Glu Asp Asn Ala Thr Val His Trp Val Leu Arg Lys Pro Ala Ala Gly Ser
TGC CCG GGC GTA GAG GAG CCG GAA AAT GCC ACT GTT CAC TGG GTG CTC AGG AAG CCG GCT GCA GGC TCC His Pro Ser Arg Trp Ala Gly Met Gly Arg Arg Leu Leu Leu Arg Ser Val Gln Leu His Asp Ser Gly
CAC CCC AGC AGA TGG GCT GGC ATG GGA AGG AGG CTG CTG CTG CGG TCG GTG CAG CTC CAC GAC TCT GGA

Fig. 3-2

```
Asn Tyr Ser Cys Tyr Arg Ala Gly Arg Pro Ala Gly Thr Val His Leu Leu Val Asp Val Pro Pro Glu
AAC TAT TCA TGC TAC CGG GCC GGC CGC CCA GCT GGG ACT GTG CAC TTG CTG GTG GAT GTT CCC CCC GAG

Glu Pro Gln Leu Ser Cys Phe Arg Lys Ser Pro Leu Ser Asn Val Val Cys Glu Trp Gly Pro Arg Ser
GAG CCC CAG CTC TCC TGC TTC CGG AAG AGC CCC CTC AGC AAT GTT GTT TGT GAG TGG GGT CCT CGG AGC

Thr Pro Ser Leu Thr Thr Lys Ala Val Leu Leu Val Arg Lys Phe Gln Asn Ser Pro Ala Glu Asp Phe
ACC CCA TCC CTG ACG ACA AAG GCT GTG CTC TTG GTG AGG AAG TTT CAG AAC AGT CCG GCC GAA GAC TTC

Gln Glu Pro Cys Gln Tyr Ser Gln Glu Ser Gln Lys Phe Ser Cys Gln Leu Ala Val Pro Glu Gly Asp
CAG GAG CCG TGC CAG TAT TCC CAG GAG TCC CAG AAG TTC TCC TGC CAG TTA GCA GTC CCG GAG GGA GAC

Ser Ser Phe Tyr Ile Val Ser Met Cys Val Ala Ser Ser Val Gly Ser Lys Phe Ser Lys Thr Gln Thr
AGC TCT TTC TAC ATA GTG TCC ATG TGC GTC GCC AGT AGT GTC GGG AGC AAG TTC AGC AAA ACT CAA ACC
```

Fig. 3-3

```
Phe Gln Gly Cys Gly Ile Leu Gln Pro Asp Pro Ala Asn Ile Thr Val Thr Ala Val Ala Arg Asn
TTT CAG GGT TGT GGA ATC TTG CAG CCT GAT CCG CCT GCC AAC ATC ACA GTC ACT GCC GTG GCC AGA AAC

Pro Arg Trp Leu Ser Val Thr Trp Gln Asp Pro His Ser Trp Asn Ser Ser Phe Tyr Arg Leu Arg Phe
CCC CGC TGG CTC AGT GTC ACC TGG CAA GAC CCC CAC TCC TGG AAC TCA TCT TTC TAC AGA CTA CGG TTT

Glu Leu Arg Tyr Arg Ala Glu Arg Ser Lys Thr Phe Thr Thr Trp Met Val Lys Asp Leu Gln His His
GAG CTC AGA TAT CGG GCT GAA CGG TCA AAG ACA TTC ACA ACA TGG ATG GTC AAG GAC CTC CAG CAT CAC

Cys Val Ile His Asp Ala Trp Ser Gly Leu Arg His Val Val Gln Leu Arg Ala Gln Glu Glu Phe Gly
TGT GTC ATC CAC GAC GCC TGG AGC GGC CTG AGG CAC GTG GTG CAG CTT CGT GCC CAG GAG GAG TTC GGG

Gln Gly Glu Trp Ser Glu Trp Ser Pro Glu Ala Met Gly Thr Pro Trp Thr Glu Ser Arg Ser Pro Pro
CAA GGC GAG AGC GAG TGG AGC GAG GCC ATG GGC ACG CCT TGG ACA GAA TCC AGG AGT CCT CCA
```

Fig. 3-4

```
Ala Glu Asn Glu Val Ser Thr Pro Met Gln Ala Leu Thr Thr Asn Lys Asp Asp Asn Ile Leu Phe
GCT GAG AAC GAG GTG TCC ACC CCC ATG CAG GCA CTT ACT ACT AAT AAA GAC GAT GAT AAT ATT CTC TTC

Arg Asp Ser Ala Asn Ala Thr Ser Leu Pro Val Gln Asp Ser Ser Val Pro Leu Pro Thr Phe Leu
AGA GAT TCT GCA AAT GCG ACA AGC CTC CCA GTG CAA GAT TCT TCA GTA CCA CTG CCC ACA TTC CTG

Val Ala Gly Gly Ser Leu Ala Phe Gly Thr Leu Leu Cys Ile Ala Ile Val Leu Arg Phe Lys Lys Thr
GTT GCT GGA GGG AGC CTG GCC TTC GGA ACG CTC CTC TGC ATT GCC ATT GTT CTG AGG TTC AAG AAG ACG

Trp Lys Leu Arg Ala Leu Lys Glu Gly Lys Thr Ser Met His Pro Pro Tyr Ser Leu Gly Gln Leu Val
TGG AAG CTG CGG GCT CTG AAG GAA GGC AAG ACA AGC ATG CAT CCG CCG TAC TCT TTG GGG CAG CTG GTC

Pro Glu Arg Pro Arg Pro Thr Pro Val Leu Val Pro Leu Ile Ser Pro Pro Val Ser Pro Ser Ser Leu
CCG GAG AGG CCT CGA CCC ACC CCA GTG CTT GTT CCT CTC ATC TCC CCA GTG TCC CCC AGC AGC CTG
```

Fig. 3-5

Gly Ser Asp Asn Thr Ser Ser His Asn Arg Pro Asp Ala Arg Asp Pro Arg Ser Pro Tyr Asp Ile Ser
GGG TCT GAC AAT ACC TCG AGC CAC AAC CGA CCA GAT GCC AGG GAC CCA CGG AGC CCT TAT GAC ATC AGC (C-Terminal)

Asn Thr Asp Tyr Phe Phe Pro Arg
AAT ACA GAC TAC TTC TTC CCC AGA

TAGCTGGCTGGTGGCACCAGCAGCCTGGACCCTGTGGATGACAAAACACAAACGGGCTCAGCAAAAGATGCTTCTCACTGCCATGCCAGCTT
ATCTCAGGGCTGTGCGGCCTTTGGCTTCACGGAAGAGCCTTGCGGAAGGTTCTACGCCAGGGGAAAATCAGCCTGCTCCAGCTGTTCAGCTGG
TTGAGGTTTCAAACCTCCCTTTCCAAATGCCCAGCTTAAAGGGTTAGAGTGAACTTGGGCCACTGTGAAGAGAACCATATCAAGACTCTTTG
GACACTCACACGGACACTCAAAAGCTGGGCAGGTTGGTGGGGCCTCGGTGTGGAGAAGCGGCTGGCAGCCCACCCCTCAACACCCTCTGCACA
AGCTGCACCCTCAGGCAGGTGGGATGGGATTTCCAGCCAAAGCCTCCTCCAGCCCGCCATGCTCCTG (3'-Terminal)

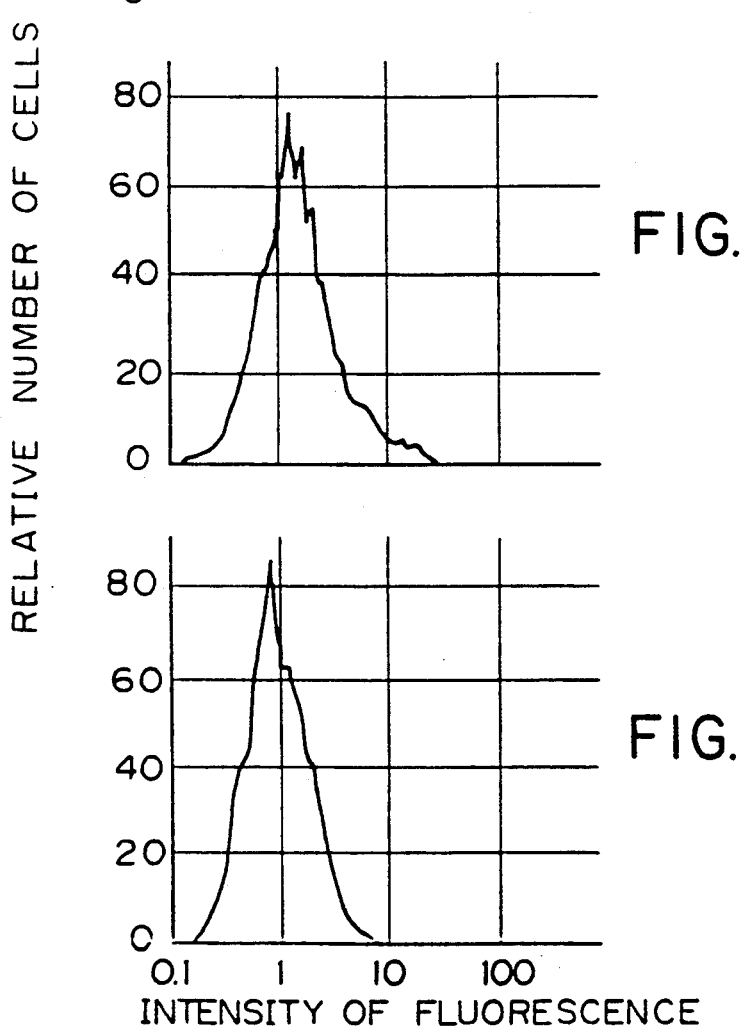

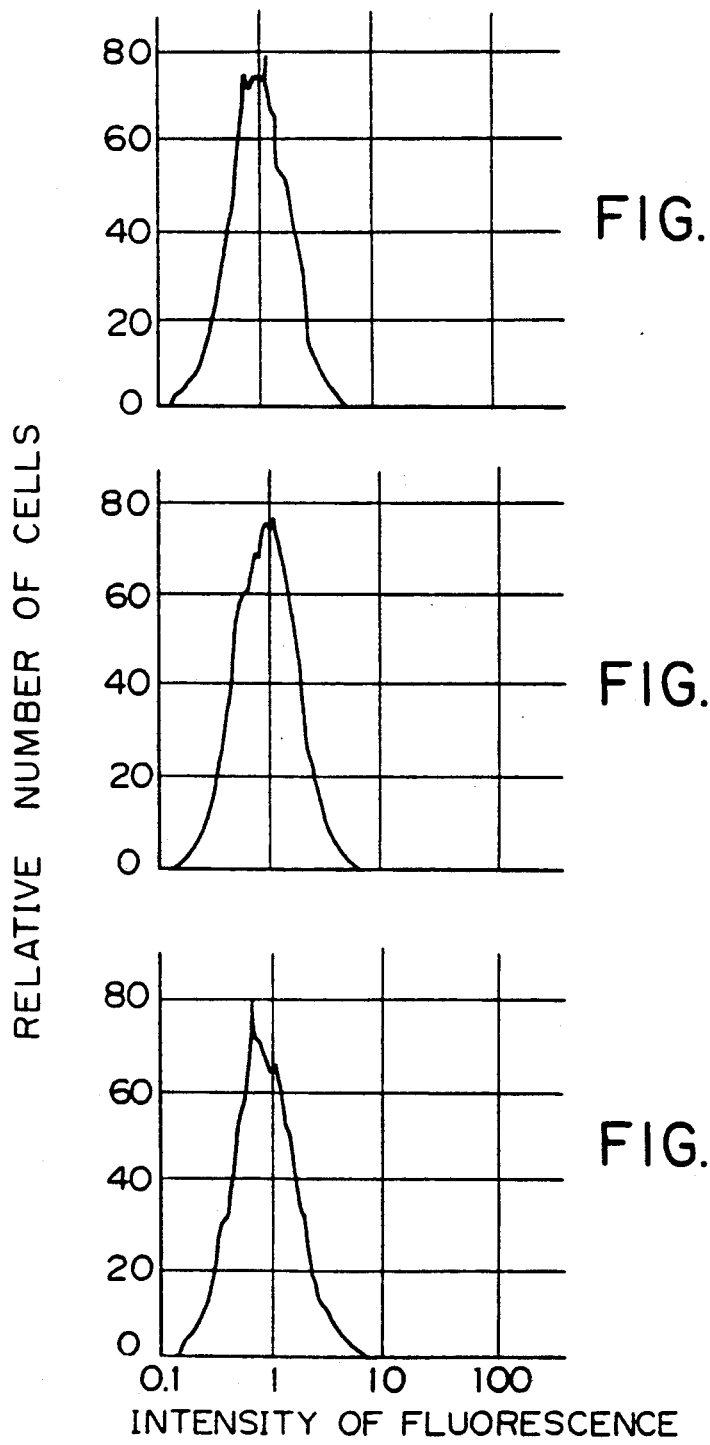

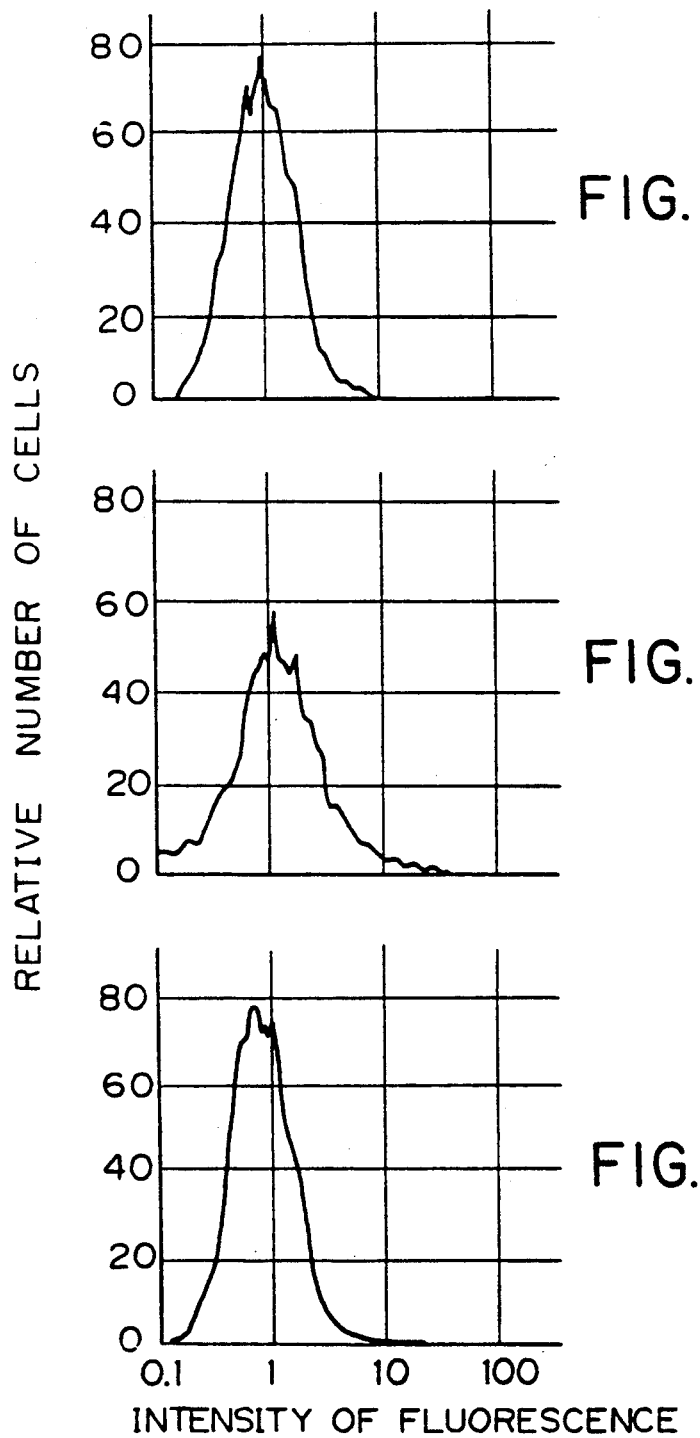

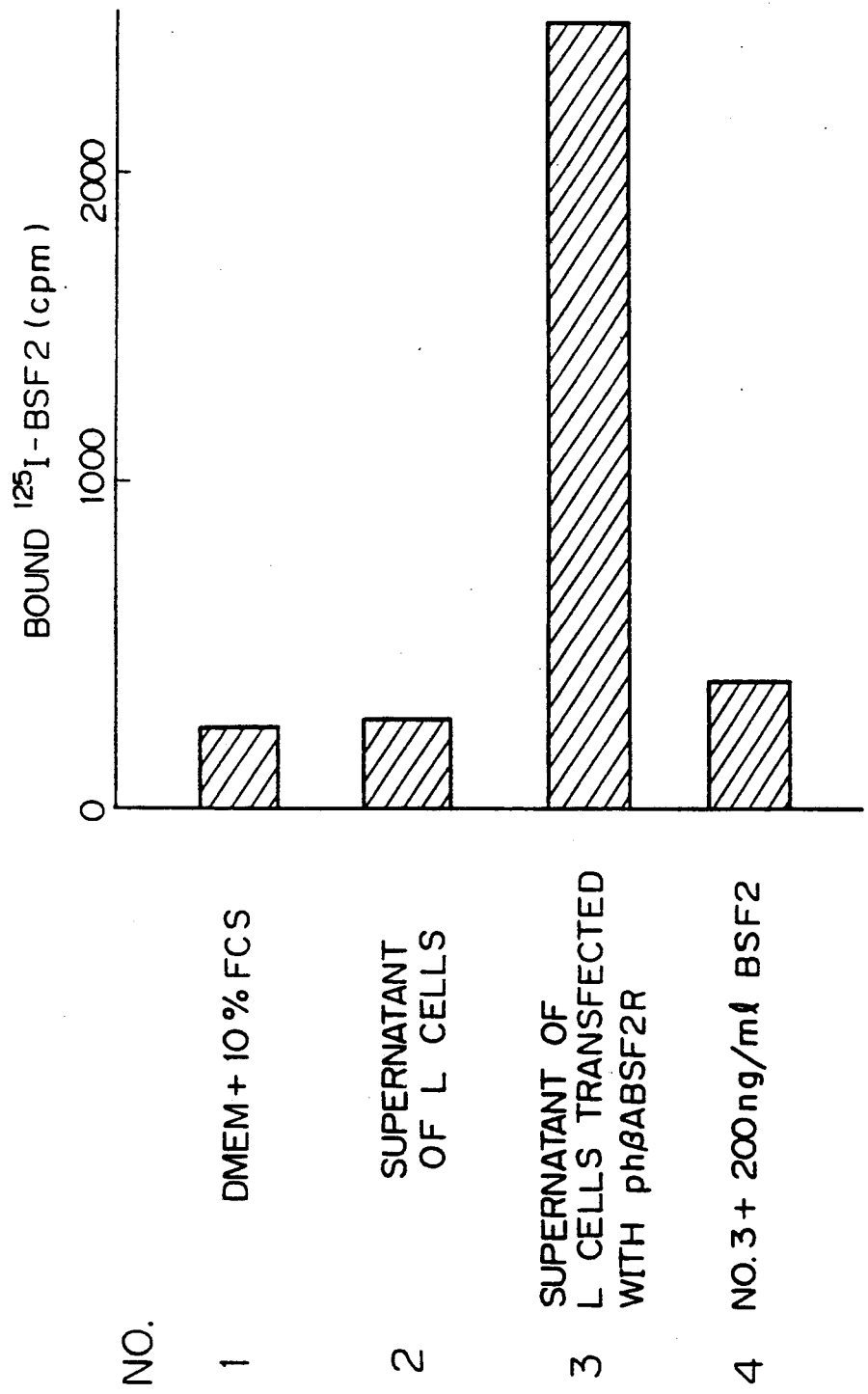

INTENSITY OF FLUORESCENCE

RECEPTOR PROTEIN FOR HUMAN B CELL STIMULATORY FACTOR-2

BACKGROUND OF THE INVENTION

1. Field of the Invention

The present invention relates to a receptor protein for a human B cell stimulatory factor-2 (hereinafter abbreviated as BSF2 receptor), a DNA sequence coding for the BSF2 receptor, and a process for the production of the BSF2 receptor using genetic engineering techniques.

2. Description of the Related Art

The B-cell stimulatory factor-2 (BSF2) is believed to be a factor which differentiates B-cells to antibody-producing cells. Recently, a cDNA coding for BSF2 was isolated, and on the basis of information relating to the DNA sequence and information relating to the partial amino acid sequence of the purified BSF2, the BSF2 was defined as a protein comprising 184 amino acid residues accompanied by a signal peptide consisting of 28 amino acid residues (T. Hirano, K. Yoshida and H. Harada et al, *Nature*, 324 73-76, 1986).

According to recent findings, the BSF2 is believed to induce B cells to produce antibodies; to stimulate the growth of hybridoma, plasmacytoma, myeloma and the like, to induce the expression of HLA class I antigens; to induce acute phase proteins on hepatocyte; and induce neuraxons (T. Kishimoto and T. Hirano, *Ann. Rev. Immunol.* 6. 485, 1985). As seen from the above, the BSF2 has various important physiological activities, and is extensively related to cell growth (Hirano et al, Summary of the 17th conference of Japan Immunology Association, pp 91,1987).

On the other hand, Hirano et al., *Proc. Natl. Acad. Sci. U.S.A.*, Vol 84, pp 228, 1987, reported the possibility that an abnormal production of BSF2 is an etiology of an immune disorder in such diseases as cardiac mixoma, cervical cancer, myeloma, chronic articular rheumatism, Castleman's syndrome, and the like. Accordingly, an inhibitor of the BSF2 would be promising as a diagnostic, prophylactic or therapeutic agent for the above-mentioned diseases.

T. Taga et al., *J. Exp. Med.* 196, pp 967, 1987, analyzed a BSF2 receptor which is found on a cell membrane and specifically linked to the BSF2, and reported the number there on a cell and the binding constant with BSF2. The BSF2 receptor released from cell surface is promising as diagnostic, prophylactic and therapeutic agents and the like, and therefore, there is great interest in the progress of research into the BSF2 receptor.

To enable further progress in the research into the BSF2 receptor and the development of diagnostic, prophylactic and therapeutic agents, the availability of a large amount of purified BSF2 receptor is essential, although the receptor can be produced in vivo in only a very small amount.

For the production of proteins, such as the BSF2 receptor, present in a very small amount in an organism, a genetic engineering technique also known as genetic manipulation is used. In this technique, a DNA sequence coding for a desired protein is cloned, the cloned DNA sequence is operatively linked with control DNA sequences such as a promoter, and the DNA sequence is inserted into a vector to construct an expression vector, which is then used to transform host cells. The transformant is cultured to produce the desired protein. To use such a genetic engineering procedure to produce a target protein, it is necessary to obtain a DNA sequence coding for the target protein. However, the gene coding for the BSF2 receptor has not yet been cloned.

SUMMARY OF THE INVENTION

Accordingly, the present invention provides a BSF2 receptor protein, a DNA sequence coding for the BSF2 receptor protein, vectors containing the DNA sequence, host cells transformed with the vector, and a process for the production of the BSF2 receptor using the transformant.

More specifically, the present invention provides an isolated receptor protein for human B cell stimulatory factor-2, capable of specifically binding to the human B cell stimulatory factor-2.

The present invention also provides a DNA coding for the above-mentioned receptor protein.

The present invention further provides expression vectors containing the above-mentioned DNA.

The present invention, moreover, provides host organisms transformed with the above-mentioned expression vector.

In addition, the present invention provides a process for the production of the receptor protein, comprising culturing the host organisms in a medium to produce the receptor protein and recovering the receptor protein from the culture.

Further, the present invention provides an antibody specifically reacting with the receptor protein.

Moreover, the present invention provides a hybridoma producing a monoclonal antibody specifically reacting with the receptor protein.

BRIEF DESCRIPTION OF THE DRAWINGS

FIGS. 3-1 to 3-5 represent a nucleotide sequence of DNA containing a region coding for the BSF2 receptor derived from a monicyte U937 cell line, and an amino acid sequence of the BSF2 receptor presumed from the nucleotide sequence. In the sequence, the single underlined part represents a hydrophobic region at the N-terminal, and the double underlined part represents a hydrophobic region at the C-terminal;

FIG. 4 represents a result of a Northern blotting analysis, wherein the presence or absence of a hybridization signal conforms to the presence or absence of the BSF2 receptor from all lines.

FIG. 5 represents a process for the construction of plasmid pΔBSF2RI.1;

FIG. 7 is graphs showing fluorescence intensity versus cell frequency in an experiment for COP cells transfected with plasmid pBSF2R.236: The meanings of A, B and C are the same as in FIG. 1;

FIG. 8 is graphs showing fluorescence intensity versus cell frequency in an experiment for COP cells transfected with plasmid pΔBSF2RI.1: The meanings of A, B and C are the same as in FIG. 1;

FIG. 9 is graphs showing fluorescence intensity versus cell frequency in an experiment for COP cells transfected with plasmid pΔBSF2RII.5: The meanings of A, B and C are the same as in FIG. 1;

FIG. 11 is a graph showing that a protein produced by plasmid phBABSF2R specifically binds to BSF2;

DESCRIPTION OF THE PREFERRED EMBODIMENTS

BSF2 receptor

Figure 1:
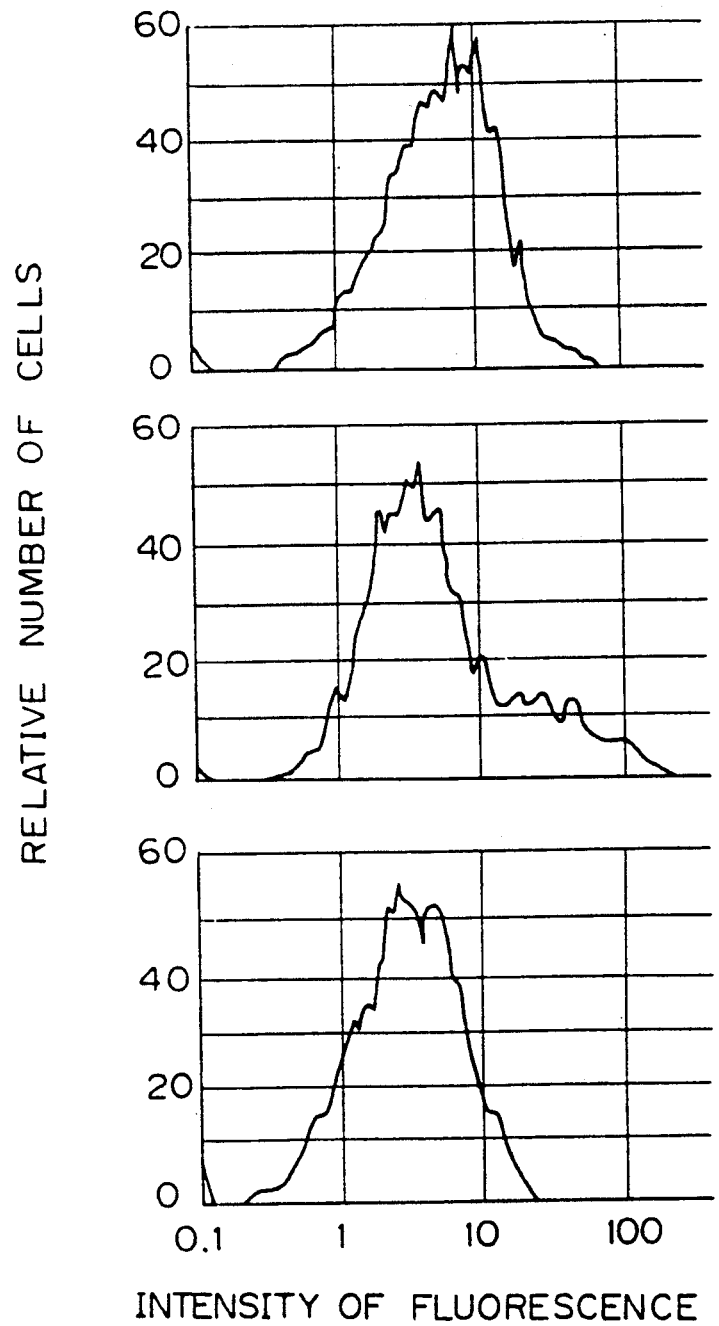
FIG. 1 represents graphs of fluorescence intensity versus cell frequency in an experiment wherein cells are stained with fluorescence via BSF2-biotin-avidin. In the figure, (A) represents a result obtained with cells transfected with a negative vector, (B) represents a result obtained with cells transfected with a vector containing the present cDNA, and (C) represents a result obtained by treating the abovementioned positively transfected cell with biotinated BSF2 in the presence of an excess amount of BSF2.
Figure 2:
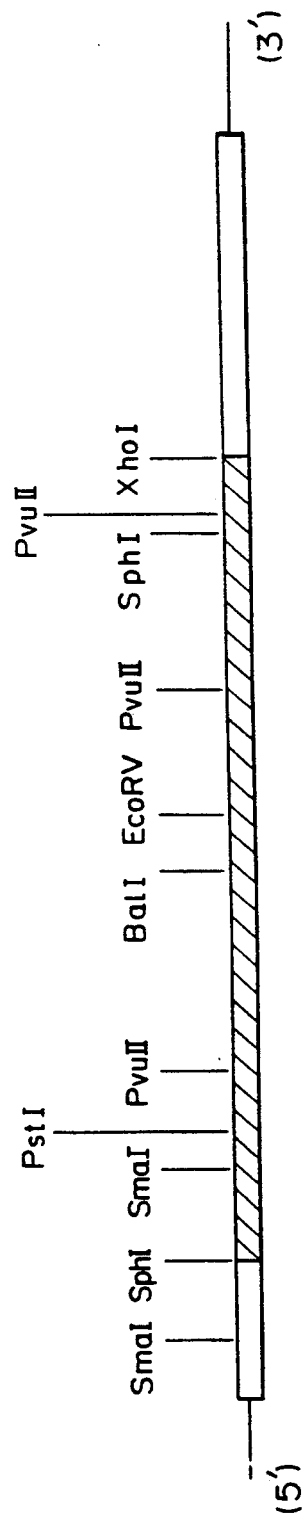
FIG. 2 represents a restriction enzyme cleavage map for a cDNA containing a DNA sequence coding for the BSF2 receptor, derived from a monocyte U937 cell line in the Example, wherein a box with oblique lines shows a region from a translation initiation codon ATG to a translation stop codon TAG.
Figure 4:
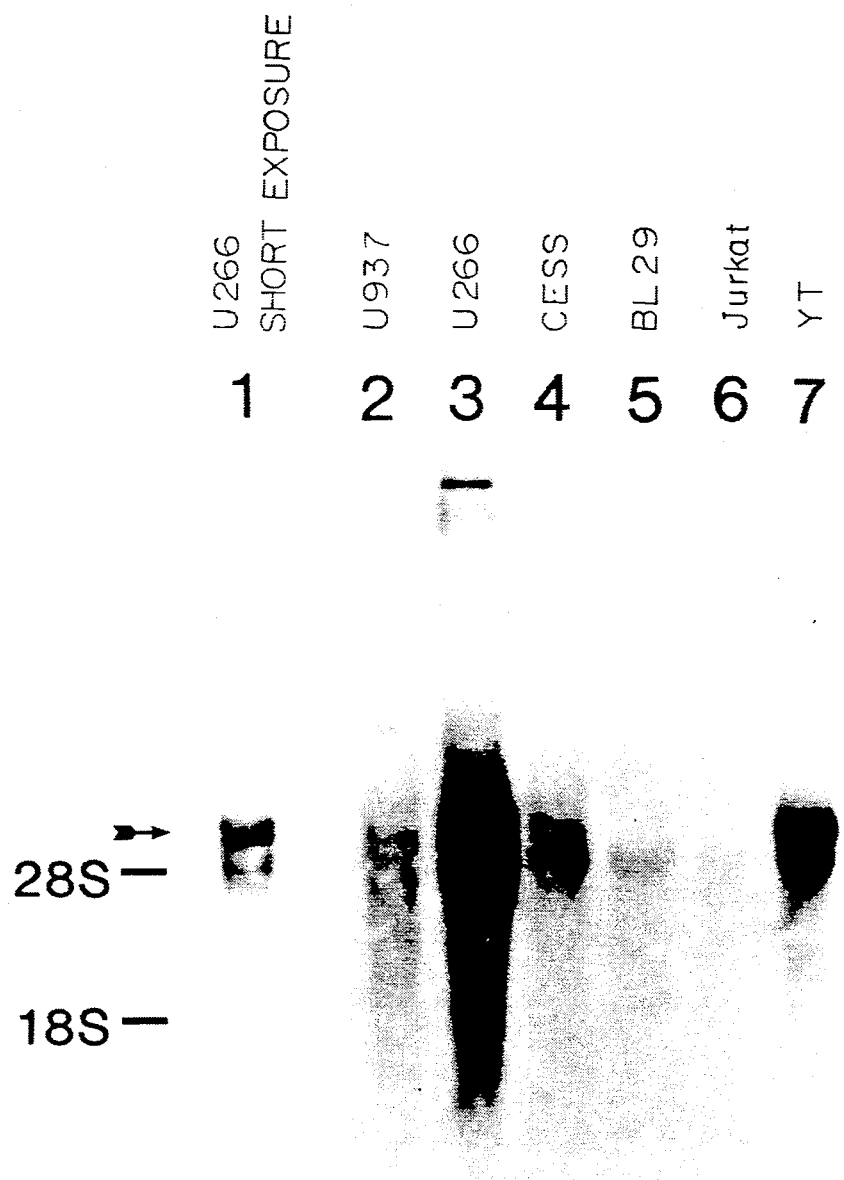

The present invention relates to a human receptor for a B cell stimulatory factor-2 (BSF2 receptor) in an isolated form. The BSF2 receptor is a protein which specifically binds to the human B cell stimulatory factor-2, and is originally produced in vivo and is present on a cell membrane. The BSF2 receptor of the present invention includes any protein with an abovementioned biological activity. In one embodiment, the BSF2 receptor protein of the present invention has the following amino acid sequence (I):

(N-terminal)
Met Leu Ala Val Gly Cys Ala Leu Leu Ala Ala Leu Leu
Ala Ala Pro Gly Ala Ala Leu Ala Pro Arg Arg Cys Pro
Ala Gln Glu Val Ala Arg Gly Val Leu Thr Ser Leu Pro
Gly Asp Ser Val Thr Leu Thr Cys Pro Gly Val Glu Pro
Glu Asp Asn Ala Thr Val His Trp Val Leu Arg Lys Pro
Ala Ala Gly Ser His Pro Ser Arg Trp Ala Gly Met Gly
Arg Arg Leu Leu Leu Arg Ser Val Gln Leu His Asp Ser
Gly Asn Tyr Ser Cys Tyr Arg Ala Gly Arg Pro Ala Gly
Thr Val His Leu Leu Val Asp Val Pro Pro Glu Glu Pro
Gln Leu Ser Cys Phe Arg Lys Ser Pro Leu Ser Asn Val
Val Cys Glu Trp Gly Pro Arg Ser Thr Pro Ser Leu Thr
Thr Lys Ala Val Leu Leu Val Arg Lys Phe Gln Asn Ser
Pro Ala Glu Asp Phe Gln Glu Pro Cys Gln Tyr Ser Gln
Glu Ser Gln Lys Phe Ser Cys Gln Leu Ala Val Pro Glu
Gly Asp Ser Ser Phe Tyr Ile Val Ser Met Cys Val Ala
Ser Ser Val Gly Ser Lys Phe Ser Lys Thr Gln Thr Phe
Gln Gly Cys Gly Ile Leu Gln Pro Asp Pro Pro Ala Asn
Ile Thr Val Thr Ala Val Ala Arg Asn Pro Arg Trp Leu
Ser Val Thr Trp Gln Asp Pro His Ser Trp Asn Ser Ser
Phe Tyr Arg Leu Arg Phe Glu Leu Arg Tyr Arg Ala Glu
Arg Ser Lys Thr Phe Thr Thr Trp Met Val Lys Asp Leu
Gln His His Cys Val Ile His Asp Ala Trp Ser Gly Leu
Arg His Val Val Gln Leu Arg Ala Gln Glu Glu Phe Gly
Gln Gly Glu Trp Ser Glu Trp Ser Pro Glu Ala Met Gly
Thr Pro Trp Thr Glu Ser Arg Ser Pro Pro Ala Glu Asn
Glu Val Ser Thr Pro Met Gln Ala Leu Thr Thr Asn Lys
Asp Asp Asp Asn Ile Leu Phe Arg Asp Ser Ala Asn Ala
Thr Ser Leu Pro Val Gln Asp Ser Ser Ser Val Pro Leu
Pro Thr Phe Leu Val Ala Gly Gly Ser Leu Ala Phe Gly
Thr Leu Leu Cys Ile Ala Ile Val Leu Arg Phe Lys Lys
Thr Trp Lys Leu Arg Ala Leu Lys Glu Gly Lys Thr Ser
Met His Pro Pro Tyr Ser Leu Gly Gln Leu Val Pro Glu
Arg Pro Arg Pro Thr Pro Val Leu Val Pro Leu Ile Ser
Pro Pro Val Ser Pro Ser Ser Leu Gly Ser Asp Asn Thr
Ser Ser His Asn Arg Pro Asp Ala Arg Asp Pro Arg Ser
Pro Tyr Asp Ile Ser Asn Thr Asp Tyr Phe Phe Pro Arg
(C-terminal)

wherein Ala represents L-alanine, Arg represents L-arginine, Asn represents L-asparagine, Asp represents L-aspartic acid, Cys represents L-cysteine, Gln represents L-glutamine, Glu represents L-glutamic acid, Gly represents glycine, His represents L-histidine, Ile represents L-isoleucine, Leu represents L-leucine, Lys represents L-lysine, Met represents L-methionine, Phe represents L-phenylalanine, Pro represents L-proline, Ser represents L-serine, Thr represents L-threonine, Trp represents L-tryptophan, Tyr represents L-threosine, Trp represents L-tryptophan, Tyr represents L-tyrosine, and Val represents L-valine.

The amino acid sequence of the present BSF2 receptor protein represented by the sequence (I) consists of 468 amino acid residues, and contains two hydrophobic regions, i.e., an N-terminal hydrophobic region from the second leucine to the 22nd proline, and C-terminal hydrophobic region from the 362nd valine to the 386th leucine. The former is expected to be a signal peptide region and the latter to be a region responsible for the penetration of the protein through a cell membrane (membrane penetration region). Note, within the present invention, a region between the signal peptide region and the membrane penetration region is designated as an "extracellular protein region", and a region of a C-terminal from the membrane penetration region is designated as an "intracellular protein region".

The BSF2 receptor of the present invention includes, in addition to the protein having the abovementioned particular amino acid sequence, any proteins or polypeptides capable of specifically binding to the BSF2. For example, modified proteins or polypeptides wherein one or more than one amino acid residue in the above-mentioned amino acid is replaced by a different amino acid residue; one or more than one amino acid residue is deleted; or one or more than one amino acid residue is added to the above-mentioned amino acid sequence, while maintaining the biological activity of the native BSF2 receptor. For example, proteins wherein an amino acid sequence and/or an amino acid residue excluding a region in the above-mentioned amino acid sequence, which relates to binding with the BSF2, are deleted or replaced with another amino acid sequence and/or an amino acid residue, and proteins wherein an amino acid sequence and/or an amino acid residue are added to the above-mentioned amino acid sequence at the N-terminal and/or C-terminal thereof. Moreover, the present BSF2 receptor may be a fusion protein wherein any one of the above-mentioned proteins is fused with another protein such as a human growth hormone, or a fragment thereof.

For example, the biologically active modified proteins wherein amino acid residues in the abovementioned amino acid sequence (I) are deleted, include proteins wherein amino acid residues near the N-terminal in the amino acid sequence (I) are deleted. An embodiment of such a modified protein has an amino acid sequence wherein an amino acid sequence from the 28th amino acid to the 109th amino acid is deleted from the amino acid sequence (I), and represented by the following amino acid sequence (II):

(N-terminal)
Met Leu Ala Val Gly Cys Ala Leu Leu Ala Ala Leu Leu
Ala Ala Pro Gly Ala Ala Leu Ala Pro Arg Arg Cys Pro
Ala Val Asp Val Pro Pro Glu Glu Pro Gln Leu Ser Cys
Phe Arg Lys Ser Pro Leu Ser Asn Val Val Cys Glu Trp Gly Pro
Arg Ser Thr Pro Ser Glu Trp Ser Leu Thr Thr Lys Ala Val
Leu Leu Val Arg Lys Phe Gln Asn Ser Pro Ala Glu Asp
Phe Gln Glu Pro Cys Gln Tyr Ser Gln Glu Ser Gln Lys
Phe Ser Cys Gln Leu Ala Val Pro Glu Gly Asp Ser Ser
Phe Tyr Ile Val Ser Met Cys Val Ala Ser Ser Val Gly
Ser Lys Phe Ser Lys Thr Gln Thr Phe Gln Gly Cys Gly
Ile Leu Gln Pro Asp Pro Pro Ala Asn Ile Thr Val Thr
Ala Val Ala Arg Asn Pro Arg Trp Leu Ser Val Thr Trp
Gln Asp Pro His Ser Trp Asn Ser Ser Phe Tyr Arg Leu
Arg Phe Glu Leu Arg Tyr Arg Ala Glu Arg Ser Lys Thr
Phe Thr Thr Trp Met Val Lys Asp Leu Gln His His Cys
Val Ile His Asp Ala Trp Ser Gly Leu Arg His Val Val
Gln Leu Arg Ala Gln Glu Glu Phe Gly Gln Gly Glu Trp
Ser Glu Trp Ser Pro Glu Ala Met Gly Thr Pro Trp Thr
Glu Ser Arg Ser Pro Pro Ala Glu Asn Glu Val Ser Thr
Pro Met Gln Ala Leu Thr Thr Asn Lys Asp Asp Asp Asn
Ile Leu Phe Arg Asp Ser Ala Asn Ala Thr Ser Leu Pro
Val Gln Asp Ser Ser Ser Val Pro Leu Pro Thr Phe Leu
Val Ala Gly Gly Ser Leu Ala Phe Gly Thr Leu Leu Cys
Ile Ala Ile Val Leu Arg Phe Lys Lys Thr Trp Lys Leu
Arg Ala Leu Lys Glu Gly Lys Thr Ser Met His Pro Pro
Tyr Ser Leu Gly Gln Leu Val Pro Glu Arg Pro Arg Pro
Thr Pro Val Leu Val Pro Leu Ile Ser Pro Pro Val Ser
Pro Ser Ser Leu Gly Ser Asp Asn Thr Ser Ser His Asn
Arg Pro Asp Ala Arg Asp Pro Arg Ser Pro Tyr Asp Ile
Ser Asn Thr Asp Tyr Phe Phe Pro Arg.
(C-terminal)

Further, other types of the biologically active modified proteins wherein amino acid residues in the abovementioned amino acid sequence (I) are deleted, include proteins wherein amino acid residues of the C-terminal portion in the amino acid sequence (I) are deleted. An embodiment of such modified protein has an amino acid sequence wherein an amino acid sequence from the 324th amino acid to the 468th amino acid are deleted, and represented by the following amino acid sequence (III):

(N-terminal)
Met Leu Ala Val Gly Cys Ala Leu Leu Ala Ala Leu Leu
Ala Ala Pro Gly Ala Ala Leu Ala Pro Arg Arg Cys Pro
Ala Gln Glu Val Ala Arg Gly Val Leu Thr Ser Leu Pro
Gly Asp Ser Val Thr Leu Thr Cys Pro Gly Val Glu Pro
Glu Asp Asn Ala Thr Val His Trp Val Leu Arg Lys Pro
Ala Ala Gly Ser His Pro Ser Arg Trp Ala Gly Met Gly
Arg Arg Leu Leu Leu Arg Ser Val Gln Leu His Asp Ser
Gly Asn Tyr Ser Cys Tyr Arg Ala Gly Arg Pro Ala Gly
Thr Val His Leu Leu Val Asp Val Pro Pro Glu Glu Pro
Gln Leu Ser Cys Phe Arg Lys Ser Pro Leu Ser Asn Val
Val Cys Glu Trp Gly Pro Arg Ser Thr Pro Ser Leu Thr
Thr Lys Ala Val Leu Leu Val Arg Lys Phe Gln Asn Ser
Pro Ala Glu Asp Phe Gln Glu Pro Cys Gln Tyr Ser Gln
Glu Ser Gln Lys Phe Ser Cys Gln Leu Ala Val Pro Glu
Gly Asp Ser Ser Phe Tyr Ile Val Ser Met Cys Val Ala
Ser Ser Val Gly Ser Lys Phe Ser Lys Thr Gln Thr Phe
Gln Gly Cys Gly Ile Leu Gln Pro Asp Pro Pro Ala Asn
Ile Thr Val Thr Ala Val Ala Arg Asn Pro Arg Trp Leu
Ser Val Thr Trp Gln Asp Pro His Ser Trp Asn Ser Ser
Phe Tyr Arg Leu Arg Phe Glu Leu Arg Tyr Arg Ala Glu
Arg Ser Lys Thr Phe Thr Thr Trp Met Val Lys Asp Leu
Gln His His Cys Val Ile His Asp Ala Trp Ser Gly Leu
Arg His Val Val Gln Leu Arg Ala Gln Glu Glu Phe Gly
Gln Gly Glu Trp Ser Glu Trp Ser Pro Glu Ala Met Gly
Thr Pro Trp Thr Glu Ser Arg Ser Pro Pro Val.
(C-terminal)

Another embodiment of the modified protein wherein a C-terminal portion of the amino acid sequence (I) is deleted, has the following amino acid sequence (IV):

(N-terminal)
Met Leu Ala Val Gly Cys Ala Leu Leu Ala Ala Leu Leu
Ala Ala Pro Gly Ala Ala Leu Ala Pro Arg Arg Cys Pro
Ala Gln Glu Val Ala Arg Gly Val Leu Thr Ser Leu Pro
Gly Asp Ser Val Thr Leu Thr Cys Pro Cly Val Glu Pro
Glu Asp Asn Ala Thr Val His Trp Val Leu Arg Lys Pro
Ala Ala Gly Ser His Pro Ser Arg Trp Ala Gly Met Gly
Arg Arg Leu Leu Leu Arg Ser Val Gln Leu His Asp Ser
Gly Asn Tyr Ser Cys Tyr Arg Ala Gly Arg Pro Ala Gly
Thr Val His Leu Leu Val Asp Val Pro Pro Glu Glu Pro
Gln Leu Ser Cys Phe Arg Lys Ser Pro Leu Ser Asn Val
Val Cys Glu Trp Gly Pro Arg Ser Thr Pro Ser Leu Thr
Thr Lys Ala Val Leu Leu Val Arg Lys Phe Gln Asn Ser
Pro Ala Glu Asp Phe Gln Glu Pro Cys Gln Tyr Ser Gln
Glu Ser Gln Lys Phe Ser Cys Gln Leu Ala Val Pro Glu
Gly Asp Ser Ser Phe Tyr Ile Val Ser Met Cys Val Ala
Ser Ser Val Gly Ser Lys Phe Ser Lys Thr Gln Thr Phe
Gln Gly Cys Gly Ile Leu Gln Pro Asp Pro Pro Ala Asn
Ile Thr Val Thr Ala Val Ala Arg Asn Pro Arg Trp Leu
Ser Val Thr Trp Gln Asp Pro His Ser Trp Asn Ser Ser
Phe Tyr Arg Leu Arg Phe Glu Leu Arg Tyr Arg Ala Glu
Arg Ser Lys Thr Phe Thr Thr Trp Met Val Lys Asp Leu
Gln His His Cys Val Ile His Asp Ala Trp Ser Gly Leu
Arg His Val Val Gln Leu Arg Ala Gln Glu Glu Phe Gly
Gln Gly Glu Trp Ser Glu Trp Ser Pro Glu Ala Met Gly
Thr Pro Trp Thr Glu Ser Arg Ser Pro Pro Ala Glu Asn
Glu Val Ser Thr Pro Met Gln Ala Ler Thr Thr Asn Lys
Asp Asp Asp Asn Ile Leu.
(C-terminal)

DNA Sequence Coding for BSF2 Receptor

DNA sequences of the present invention include those coding for any one of the above-mentioned BSF2 receptor proteins.

In an embodiment, the present DNA sequences are those coding for the amino acid sequence represented by the sequence (I). Due to the degeneracy of codons, there may be many particular DNA sequences. The DNA sequence of the present invention can be prepared by any conventional procedure. For example, a nucleotide sequence of the present DNA can be designed according to the above-mentioned amino acid sequence, considering codons frequently used in a host cell which is chosen for the production of the BSF2 receptor protein and can be chemically synthesized. Alternatively, the desired DNA may be prepared from a genome of BSF2 receptor producing cells.

Most conveniently, however, a DNA fragment containing gene coding for the BSF2 receptor can be prepared as cDNA from the BSF2 receptor producing cells, such as the NK cell YT, monocyte cell line U937, myeloma cell line U266, B cell CESS. Namely, mRNA is extracted from cultured cells of any of the above-mentioned cells lines according to a conventional procedure, and a cDNA library is constructed on the basis of the mRNA.

The cDNA library may be then screened using an oligonucleotide probe corresponding to a part of the above-mentioned sequence (II). Alternatively, and preferably, according to the present invention, the cDNA library can be screened without a probe. In this procedure, the cDNA library is used to prepare vectors containing cDNA, which are then used to transform animal cells. The cells are then cultured, and the cultured cells are treated with a biotinated BSF2 preparation. During this procedure, cells which have expressed the BSF2 receptor bind the BSF2 moiety of the biotinated BSF2. The treated cells are then treated with avidin conjugated with fluorescein isocyanate to react the biotin moiety fixed to the cells with the avidin moiety of the avidin-fluorescein isocyanate conjugate. Subsequently, cells which have expressed the BSF2 receptor, and therefore carry fluorescein isocyanate on their surface, are separated and selected by a cell sorter. The desired cDNA coding for the BSF2 receptor is then extracted from the selected cells. An embodiment of a cDNA thus obtained has the following sequence (V):

wherein one or more than one nucleotide in the above-mentioned sequence (V) is replaced by other nucleotides, or wherein one or more than one codon is added to or deleted from the sequence (V), still coding for a protein capable of binding to the BSF2.

For example, a DNA coding for a shortened or truncated BSF2 receptor protein can be prepared by cleaving the above-mentioned cDNA having the nucleotide sequence (V) with an appropriate restriction enzyme to delete a portion of the nucleotide sequence and religating the cleaved DNA fragments if necessary via an appropriate linker.

For example, a vector containing the cDNA having the nucleotide sequence (V) can be manipulated according to Example 6, to prepare a vector containing a DNA coding for a protein consisting of an amino acid sequence 1 to 123 and an amino acid sequence 343 to 468 of the above-mentioned amino acid sequence (I). Similarly, a vector containing a DNA coding for a protein consisting of an amino acid sequence 1 to 27 and amino acid sequence 110 to 468 of the amino acid sequence (I) can be prepared.

In another embodiments any nucleotide in the above-mentioned vector can be deleted or replaced by another nucleotide by site-specific invitro-mutagenesis. In this manner, a translation stop codon can be introduced at any position of the cDNA coding for BSF2 receptor protein to obtain a DNA coding for any C-terminal truncated BSF2 receptor protein. For example, as shown in Example 11, a vector containing a DNA coding for a protein having an amino acid sequence 1 to 344 of the amino acid sequence (I) is constructed. According to a similar procedure, a vector containing DNA (5'-terminal)
```
ATG CTG GCC GTC GGC TGC GCG CTG CTG GCT GCC CTG CTG
GCC GCG CCG GGA GCG GCG CTG GCC CCA AGG CGC TGC CCT
GCG CAG GAG GTG GCA AGA CGC GTG CTG ACC AGT CTG CCA
GGA GAC AGC GTG ACT CTG ACC TGC CCG GGG GTA GAG CCG
GAA GAC AAT GCC ACT GTT CAC TGG GTG CTC AGG AAG CCG
GCT GCA GGC TCC CAC CCC AGC AGA TGG GCT GGC ATG GGA
AGG AGG CTG CTG CTG AGG TCG GTG CAG CTC CAC GAC TCT
GGA AAC TAT TCA TGC TAC CGG GCC GGC CGC CCA GCT GGG
ACT GTG CAC TTG CTG GTG GAT GTT CCC CCC GAG GAG CCC
CAG CTC TCC TGC TTC CGG AAG AGC CCC CTC AGC AAT GTT
GTT TGT GAG TGG GGT CCT CGG AGC ACC CCA TCC CTG ACG
ACA AAG GCT GTG CTC TTG GTG AGG AAG TTT CAG AAC AGT
CCG GCC GAA GAC TTC CAG GAG CCG TGC CAG TAT TCC CAG
GAG TCC CAG AAG TTC TCC TGC CAG TTA GCA GTC CCG GAG
GGA GAC AGC TCT TTC TAC ATA GTG TCC ATG TGC GTC GCC
AGT AGT GTC GGG AGC AAG TTC AGC AAA ACT CAA ACC TTT
CAG GGT TGT GGA ATC TTG CAG CCT GAT CCG CCT GCC AAC
ATC ACA GTC ACT GCC GTG GCC AGA AAC CCC CGC TGG CTC
AGT GTC ACC TGG CAA GAC CCC CAC TCC TGG AAC TCA TCT
TTC TAC AGA CTA CGG TTT GAG CTC AGA TAT CGG GCT GAA
CGG TCA AAG ACA TTC ACA ACA TGG ATG GTC AAG GAC CTC
CAG CAT CAC TGT GTC ATC CAC GAC GCC TGG AGC GGC CTG
AGG CAC GTG GTG CAG CTT CGT GCC CAG GAG GAG TTC GGG
CAA AGC GTG TGG AGC GAG TGG AGC CCG GAG GCC ATG GGC
ACG CCT TGG ACA GAA TCC AGG AGT CCT CCA GCT GAG AAC
GAG GTG TCC ACC CCC ATG CAG GCA CTT ACT ACT AAT AAA
GAC GAT GAT AAT ATT CTC TTC AGA TCT GCA AAT GCG
ACA AGC CTC CCA GTG CAA GAT TCT TCT TCA GTA CCA CTG
CCC ACA TTC CTG GTT GCT GGA GGG AGC CTG GCC TTC GGA
ACG CTC CTC TGC ATT GCC ATT GTT CTG AGG TTC AAG AAG
ACG TGG AAG CTG CGG GCT CTG AAG GAA GGC AAG ACA AGC
ATG CAT CCG CCG TAC TCT TTG GGG CAG CTG GTC CCG GAG
AGG CCT CGA CCC ACC CCA GTC CTT GTT CCT CTC ATC TCC
CCA CCG GTG TCC CCC AGC AGC CTG GGG TCT GAC AAT ACC
TCG AGC CAC AAC CGA CCA GAT GCC AGG GAC CCA CGG AGC
CCT TAT GAC ATC AGC AAT ACA GAC TAC TTC TTC CCC AGA.
```
(3'-terminal)

The DNA sequence of the present invention includes, in addition to the above-mentioned sequence (V), those coding for a protein having an amino acid sequence 1 to 323 of the amino acid sequence (I) is constructed.

Next, the DNA, for example, cDNA, coding for the BSF2 receptor is linked with DNA sequences necessary for the expression of the BSF2 receptor in a host. Such DNA sequences include a promoter, start codon and stop codon of the transcription and translation, and are selected depending on the nature of the host used. Among the DNA sequences necessary for the expression, the promoter is important. A promoter which can be used as a bacterial host includes known promoters such as β-lactamase and lactose promoter, tryptophan promoter, and hybrid promoters derived therefrom. For a yeast host, for example, GAL4 promoter can be used.

In addition to the above-mentioned DNA sequences necessary for the expression of the BSF2 receptor, preferably another control sequence such as a ribosome binding site is linked with the DNA coding for the BSF2 receptor.

The DNA sequence coding for the BSF2 receptor is linked with the above-mentioned DNA sequences necessary for the expression of the BSF2 receptor in a manner such that the DNA sequence coding for BSF2 receptor can be transcribed and transformed in a selected host under the control of the DNA sequences necessary for the expression of the BSF2. The linkage is usually carried out by ligation via cohesive ends or blunt ends, preferably via cohesive ends, of the DNA sequences to be linked.

According to a preferable embodiment of the present invention, the BSF2 receptor protein is expressed as a fusion protein with a partner protein, such as a human growth hormone protein. In such a case, the 5'-end of the DNA sequence coding for the BSF2 receptor is ligated in a reading frame with the 3'-end of a DNA sequence coding for the partner protein, such as the human growth hormone protein.

Expression Vector

Expression vectors of the present invention contain, in addition to the above-mentioned DNA sequence coding for the BSF2 receptor linked with the DNA sequences necessary for the expression of the BSF2 receptor, an origin of replication and at least one selective maker gene. These components of the expression vector are selected in accordance with the host organism used. For example, when a bacterium such as E. coli is used as a host, an origin of replication is derived from conventional E. coli plasmids such as pBR322, pBR337 or the like. For a yeast host, the origin of replication is preferably Cal4 or α-Factor. Where animal cells such as mammalian cells are used as host cells, the origin of replication is preferably derived from a virus such as the SV40 virus.

The choice of selective maker gene also depends on the host organisms. Selective maker genes useful for bacterial hosts are, for example, ampicillin resistant gene, tetracycline resistant gene, or the like.

Host Organism

In the present invention, any conventional host organisms including microorganisms, and animal cells can be used. As the bacterial hosts, various strains of E. coli such as K-12, x-1776, w-3110, MC 1009 and the like are typically used. Moreover, Bacillus such as Bacillus subtilis, Salmonella typhimurium, Serratia marcescens, Pseudomonas, and certain thermophilic bacteria can be used. As the yeast host, for example, Saccharomyces, such as Saccharomyces cerevisiae can be used, and as the mammalian host, cell lines such as COS cells derived from the renal fibroblast of a monkey, CHO cells (Chinese hamster ovary cells), WI38, BHK, 3T3, VERO, HeLa, etc., can be used.

Production of BSF2 Receptor Using Transformant

The BSF2 receptor is produced by culturing transformant cells prepared by transforming the abovementioned host with the above-mentioned expression vector to express the BSF2 receptor, and recovering the BSF2 receptor from the culture. The expression is induced by de-repression or activation of the promoter in the expression vector. Usually, the transformant cells are grown to a predetermined density under the condition wherein the promoter is repressed, after that the promoter is de-repressed or activated to express the BSF2 receptor. For this purpose, for example, indole acetic acid (IAA) for trp promoter, isopropyl-β-D-thiogalactopyranoside (IPTG) for tac promoter is used.

Antibodies to the BSF2 Receptor

The present invention also provides antibodies to the BSF2 receptor. The present antibodies include any antibodies specifically bound to the BSF2 receptor produced by any of the above-mentioned BSF2 receptor producing cell lines, or to any of the above-mentioned recombinant BSF2 receptors. The antibodies may be polyclonal or monoclonal and may be produced by human, mouse, rabbit, sheep or goat, or by hybridoma derived from there animals. As antigens used to immunize animals to produce polyclonal antibodies, or to prepare hybridoma for the production of monoclonal antibodies, cells expressing the BSF2 receptor, BSF2 receptor proteins produced by the above-mentioned cell lines, and various recombinant BSF2 receptor proteins can be used.

The present polyclonal and monoclonal antibodies can be produced according to a procedure known per se.

According to the present invention, the DNA sequence coding for the BSF2 receptor protein, expression vectors containing the DNA sequence, and the transformant containing the DNA sequence are provided. By using the transformant, a large amount of the BSF2 receptor protein can be produced, which provides an opportunity to develop prophilactic and therapeutic pharmaceuticals as well as diagnostic agents relating to deseases or disorders associated with an abnormal production of the BSF2. Moreover, the availability of the BSF2 receptor protein in a purified form will accelerate the studies of an immune mechanism with which the BSF2 or BSF2 receptor is concerned.

Moreover, the DNA sequence per se. may be useful as a probe for screening related genes.

EXAMPLES

The present invention will now be further illustrated by but is by no means limited to the following examples.

Example 1

Confirmation of Presence of BSF2 Receptor on Some Cell Lines

The BSF2 receptor specifically binds to BSF2 (T. Taga et al., *J. Exp. Med.*, 166, pp 967, 1987). By using this property, the NK cell YT, monocyte U937 cell line, myeloma U266 cell line, T-cell Jurkat cell line, B-cell CESS cell line, and B-cell BL29 cell line are tested for possession of the BSF2 receptor.

Cells of each of these cell lines were cultured in Dulbecco's Modified Eagle's Medium (D-MEM; Dulbeccos) supplemented with 10% fetal calf serum (FCS) according to a conventional procedure. The BSF2 was prepared according to a process described in Nature 324 (6) pp 73-76, 1986. Note, the BSF2 can be also prepared according to a process disclosed in Japanese Unexamined Patent Publication No. 61-24697.

Next, the BSF2 thus prepared was labeled with $^{125}I$ according to a procedure described by T. Taga et al., *J. Exp. Med.*, 166, 967, 1987. The $^{125}I$-labeled BSF2 was reacted with the above-mentioned cultured cells according to a method of Taga et al., supra. After the $^{125}I$-labeled BSF2 non-specifically associated with the cells was washed away, the $^{125}I$ which specifically binds to the BSF2 producing cells was detected by a scintillation counter. As a result, the presence of the BSF2 receptor was determined on cells of all of the cell lines tested, except for the B-cell BL29 cell line and T-cell Jurkat cell line.

Example 2

Isolation of mRNA

The isolation of mRNA was carried out according to Manistis et al., *Molecular Cloninc*, Cold Spring Harbor Laboratory, 1982.

Monocyte U937 (ATCC-CRL-1593) was cultured by the same procedure as described in Example 1, and the cultured cells were washed with physiological saline. The washed cells were suspended in a solution of 50% guanidineisothiocyanate, and the solution was subjected to cesium chloride density-gradient centrifugation using 5.7M cesium chloride and 2.7M cesium chloride at 32000 rpm for 20 hours to obtain a mixture of m-RNA. The mRNA was suspended in a sodium lauroyl sarcosinate solution, and purified by phenol extraction and ethanol precipitation.

Example 3

Construction of cDNA Library

The mRNA fraction thus obtained was used as a temperate for a synthesis of cDNA. The synthesis was carried out using a cDNA synthesis kit (Applied Biosystems) to obtain a cDNA library.

Example 4

Cloninc of Desired cDNA Clone

As a host, COS cells (COS-7 cells) were used; and as a vector compatible to the COS cells, a CDM8 vector described by Brian Seed, *Nature* 329, pp 840, 1987 was used. The CDMS vector contains a cytomegalovirus promoter and an origin of replication from the SV40 virus, as well as a restriction enzyme cleavage site downstream of the cytomegalovirus promoter.

Excised cDNA's were ligated to the CDM8 vector which had been digested with a restriction enzyme Bst X 1, and the resulting vectors containing a cDNA insert were used to transfect COS cells. Namely, COS cells were cultured in D-MEM supplemented with 10% FCS and transfection was carried out according to a DEAE-dextran method, and the transfected COS cells were further cultured for two days. To the cultured COS cells was added a staining buffer (RPMI 1640 containing 2% FCS, 0.1% NaN$_3$) supplemented with biotinated BSF2, and the mixture was incubated at 37° C. for two hours to allow binding of the BSF2 moiety of the biolinated BSF2 with the BSF2 receptor expressed on the cultured COS cells. The treated cells were then washed twice with the staining buffer (without the biotinated BSF2), and to the washed cells was added avidin conjugated with fluorescein isocyanate (FITC) to allow binding of the avidin moiety of the avidin-FITC conjugate with the biotin moiety fixed to the cell. The treated cells were then washed three times with the staining buffer.

After dead cells were eliminated by adding propidium iodide (PI), fluorescence-labeled COS cells were detected and isolated using a Fluorescein Activated Cell Sorter FACS; Becton Dickinson).

For comparison, the COS cells transfected with a vector not containing cDNA were treated according to the same procedure as described above.

Moreover the COS cells transfected with a cDNA-containing vector were treated with the biotinated BSF2 in the presence of an excess amount of free BSF2 to allow competition between the biotinated BSF2 and the free BSF2 for binding to BSF2 receptor expressed on the COS cells. After the biotinated BSF2-treated COS cells were treated with the FITC-avidin according to the same procedure as described above, the cells were analyzed by the FACS, and the results were as set forth in FIG. 1, wherein the abscissa axis represents the fluorescence intensity, and the ordinates axis represents the frequency of the number of cells carrying different fluorescence-intensities. In the Figure, A represents a result obtained from cells transfected with a vector not containing cDNA, B represents a result obtained from cells transfected with vectors containing a cDNA according to the present invention, and C represents a result obtained from cells transfected with vectors containing BSF2 receptor cDNA, but treated with the biotinated BSF2 in the presence of a excess amount of free BSF2.

The graph B shows the presence of cells having high fluorescence intensity, revealing that a population of cells transfected with vectors containing cDNA prepared according to the present invention contains a significant ratio of cells which produce a substance capable of binding to the BSF2. On the other hand, as seen from graph C, a population of cells treated with the biotinated BSF2 under a competitive condition with an excess amount of free BSF2 does not contain cells having a high fluorescence intensity, revealing that the binding of the biotinated BSF2 with the COS cells is BSF2-specific.

From the cells having a high fluorescence intensity, vectors were extracted and were used to transform *E. coli* MC1009 (ATCC 33760), and the transformants were cultured to amplify vectors containing a cDNA insert coding for the BSF2 receptor.

One vector thereamong was then chosen for further experiments and designated as pBSF2R.236.

The plasmid pBSF2R.236 partially digested with XhoI to obtain a DNA fragment containing a nucleotide sequence coding for an entire BSF2 receptor protein, and the DNA fragment was inserted to the Sal I site of plasmid pIBI76 (commercially available from IBI) to construct plasmid pIBIBSF2R. *Escherichia coli* containing the plasmid pIBIBSF2R was deposited with the Fermentation Research Institute Agency of Industrial Science and Technology, 1-3, Higashi 1-chome, Tsukuba-shi, Ibaraki-ken, Japan, under the Budapest treaty, on Jan. 9, 1989, as FERM BP-2232.

The plasmid pIBISF2R can be cleaved with a suitable restriction enzyme(s) by a conventional procedure to obtain a DNA fragment containing a nucleotide sequence coding for a BSF2 receptor protein, and the DNA fragment can be used to construct further plasmids.

Example 5

Analysis of cDNA

The vector DNA pBSF2R.236 prepared in Example 4 was digested with a restriction enzyme to excise the cDNA insert coding for the BSF2, and the determination of a restriction enzyme cleavage map and nucleotide sequence was carried out according to the M13 method of, J. Messing, *Methods in Enzymol.* vol. 101, pp 20, 1983.

The results are set forth in FIGS. 2 and 3-1 to 3-5. The DNA coding for the BSF2 receptor consists of 1404 base pairs flanked by a translation start codon ATG at the 5,-terminal and a translation stop codon TAG at the 3,-terminal.

Example 6

Confirmation of cDNA Coding for BSF2 Receptor

To confirm that the cloned cDNA codes for the target BSF2 receptor protein, the above-mentioned cell lines, i.e., NK cell line YT, monocyte cell line U937, myeloma cell line U266, T-cell Jurkat, B-cell CESS, and B-cell BL29, were cultured and mRNA was extracted from each culture and purified according to the same procedure as described in Example 2.

The purified mRNA was concentrated by oligo-dT resin (Boehringer), and 1 $\mu$g of the concentrated mRNA was subjected to 0.8% agarose gel electrophoresis and transferred to a nitrocellulose filter by Northern blotting.

On the other hand, the vector DNA prepared in Example 4 was digested with a restriction enzyme XhoI to excise the DNA fragment coding for the BSF2 receptor, which was then nick-translated to prepare a probe.

For hybridization, the above-mentioned Northern-blotted nitrocellulose sheet was placed in contact with a hybridization buffer comprising 50% formaldehyde, 5×Denhart (1×Denhart=0.02 g/100 ml Ficoll polyvinyl pyrrolidone and 0.02 g/ml bovine serum albumin), 5×SSC (1×SSC=8.77 g/l NaCl and 4.41 g/l sodium citrate, pH 7.0), and 10 $\mu$g/ml salmon sperm DNA supplemented with $1 \times 10^7$ cpm/ml of the above-mentioned probe, at 42° C. for 24 hours.

After the hybridization, the nitrocellulose sheet was washed twice in 1/10 SSC at 50° C. for 20 minutes each to eliminate the probe non-specifically associated with the nitrocellulose sheet, and then dried. The sheet was exposed to an X-ray film for autoradiography, and the results were as set forth in FIG. 4.

As seen from the Figure, mRNA's extracted from monocyte cell line U937, myeloma cell line U266, B-cell line CESS, and NK cell line YT, which were previously confirmed as expressing the BSF2 receptor in Example 1, hybridized with the cloned cDNA. On the other hand, mRNA's extracted from the B-cell line BL29 and T-cell line Jurkat, which were previously confirmed as not expressing the BSF2 receptor, did not hybridize with the cloned DNA. This result supports the fact that the cloned cDNA of the present invention actually codes for the BSF-2 receptor protein.

Note, T. Taga, supra, disclosed the number of BSF2 receptor per cell for some cell lines, as follows:

| Cell line | Number of cells on cell membrane |
| --- | --- |
| U937 | $3 \times 10^3$/cell |
| U266 | $2 \times 10^4$/cell |
| CESS | $3 \times 10^3$/cell |
| BL29 | negative |
| Jurkat | negative |
| YT | $5 \times 10^3$/cell |

The T. Taga et al. result also supports the abovementioned conclusion.

FIG. 3 represents, in addition to the DNA sequence of the present invention, a presumed amino acid sequence of the present BSF2 receptor consisting of 468 amino acid residues whose N-terminal amino acid is methionine corresponding to the translation start codon. The amino acid sequence contained two hydrophobic regions, one of which was positioned at the N-terminal side and was considered to be a signal peptide, and another of which was positioned on the C-terminal side and was considered to be a region responsible for the penetration of the protein through the cell membrane. This supports the assumption that the BSF-2 receptor penetrates the cell membrane and reaches the inside of the cell.

Example 6

Figure 5:
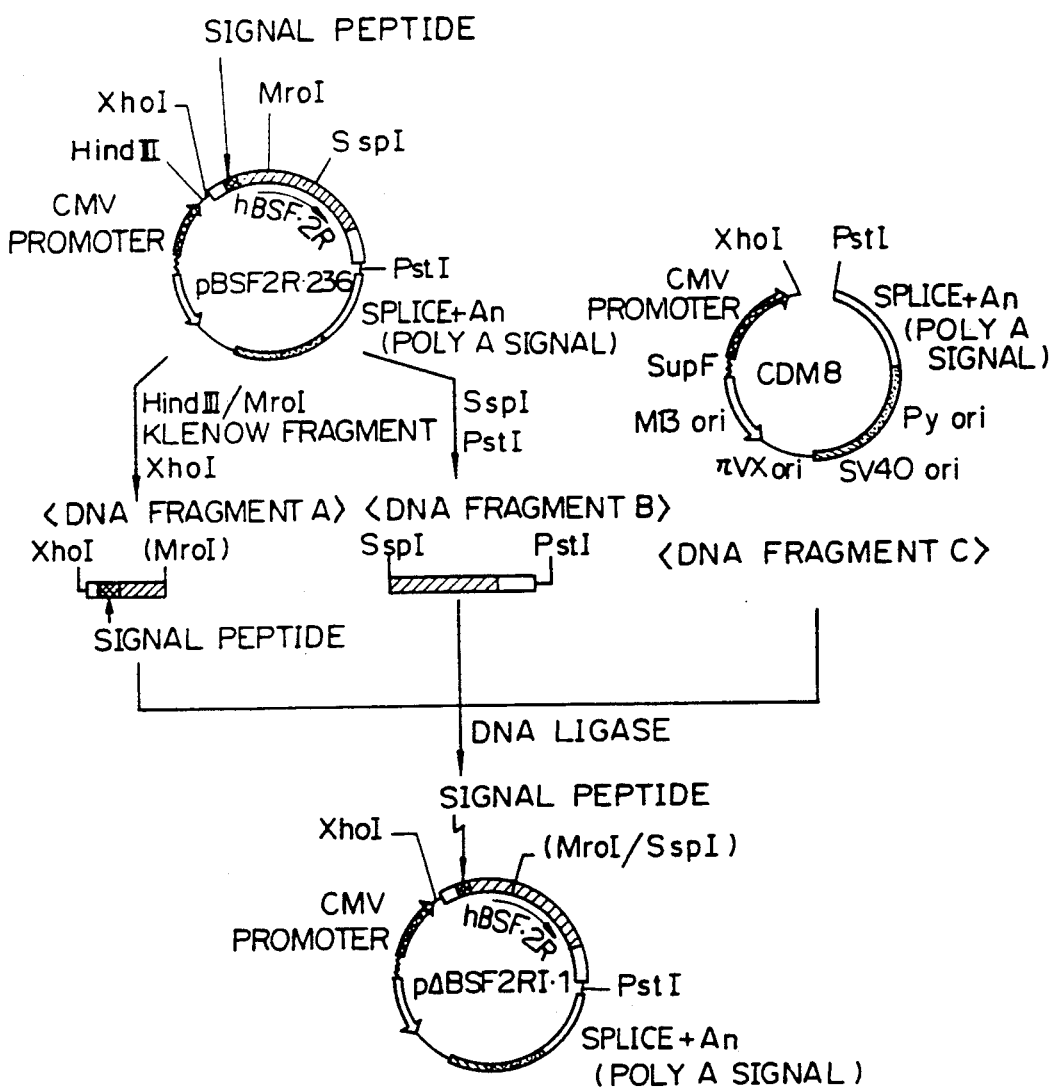

Construction of Plasmid pΔBSF2RI.1 (FIG. 5)

To prepare a plasmid containing a DNA coding for a modified BSF2 receptor protein wherein a central portion of the native protein is deleted, the plasmid pBSF2R.236 prepared in Example 4 and containing a cDNA coding for an entire BSF2 receptor protein was used.

The plasmid pBSF2R.236 was cleaved with Hind III and MroI, and a generated DNA fragment was blunt-ended with a Klenow fragment of DNA polymerase, and cleaved with XhoI to obtain a DNA fragment A. Further, pBSF2R.236 was cleaved with SspI and PstI to obtain an 800 bp DNA fragment B. Still further, a CDM8 vector was cleaved with XhoI and PstI, and treated with BAP to obtain a vector fragment C. The above-mentioned fragments A, B and C were then ligated using a ligase, and the ligation mixtures were used to transform *E. coli* MC1061/P3, and a colony resistant to 125 $\mu$g/ml ampicillin and 75 g/ml tetracycline was selected as a desired clone, from which a plasmid was obtained, and designated pΔBSF2RI.1.

This plasmid contains a DNA coding for a protein consisting of amino acids 1 to 123 and 343 to 468 in the amino acid sequence (1), and lacking a DNA portion coding for amino acids 124 to 342.

Example 7

Figure 6:
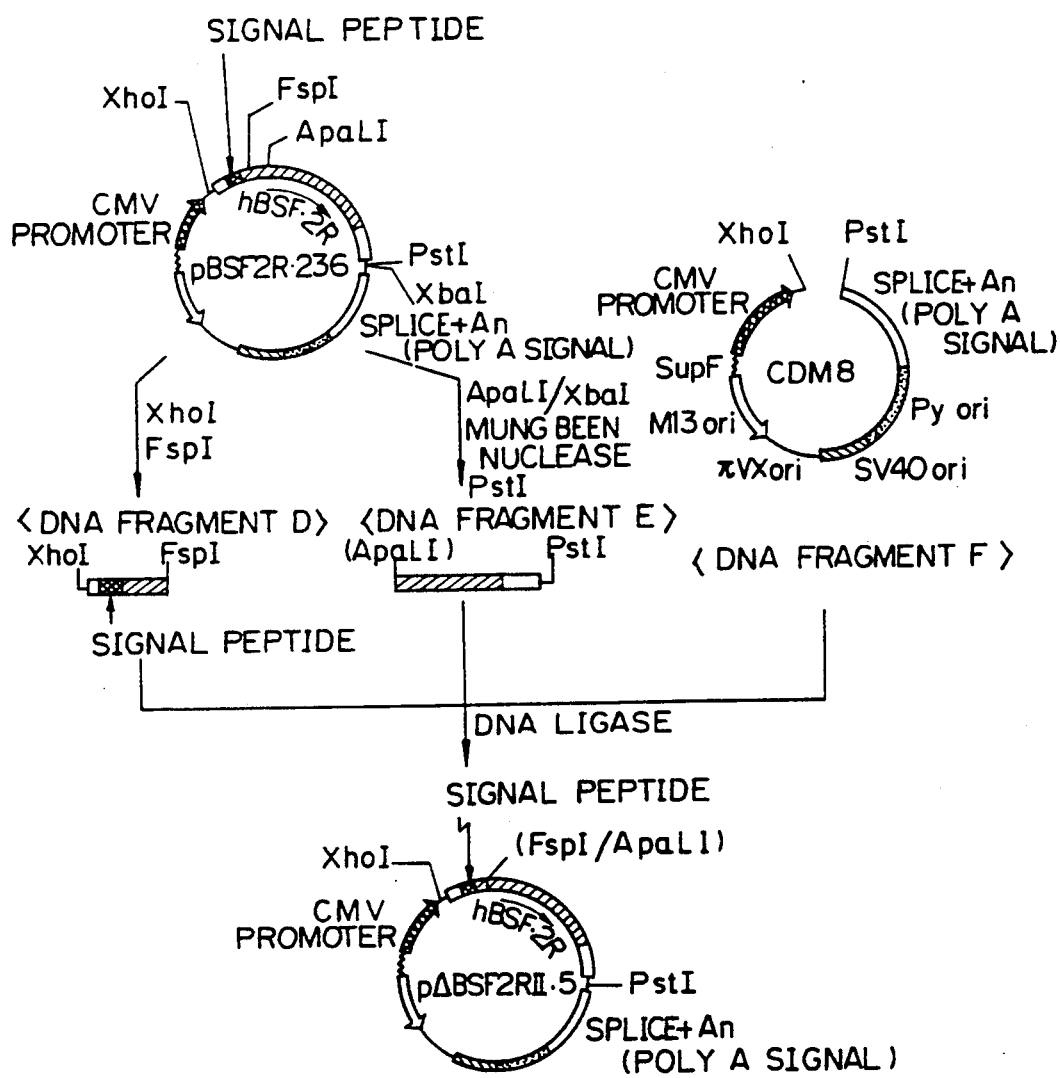
FIG. 6 represents a process for the construction of plasmid pΔBSF2RII.5.

Construction of Plasmid pΔBSF2RII.5 (FIG. 6)

To prepare a plasmid containing a DNA coding for a modified BSF2 vector protein, wherein a portion near the N-terminal of the native BSF2 receptor protein was deleted, the plasmid pBSF2R.236, prepared in Example 4, containing a cDNA coding for an entire BSF2 receptor protein, was used.

The plasmid pBSF2R.236 was cleaved with XhoI and FspI to isolate a 450 bp DNA fragment D. Further, pBSF2R.236 was cleaved with ApaLI and XbaI to isolate a 1.5 kbp DNA fragment, which was then treated with Mung bean nuclease, and cleaved with PstI to obtain a DNA fragment E. Moreover, a CDM8 vector was cleaved with XhoI and PstI, and treated with BAP to obtain a vector DNA fragment F. Next, the above-prepared DNA fragments D, E, and F were ligated using DNA ligase. The ligation mixture was used to transform E. coli MC1061/P3, and a colony resistant to 125 μg/ml ampicillin and 75 μg/ml tetraagcline was selected to obtain a desired clone, from which a plasmid was obtained and designated pΔBSF2RII.5.

This plasmid contained a DNA coding for protein consisting of amino acids 1 to 27 and 110 to 468 of the amino acid sequence (I), and lacking a DNA portion coding for amino acids 28 to 109.

Example 8

Confirmation of Expressions of BSF2 Receptor Protein

Plasmid pBSF2R.236 constructed in Example 4, plasmid pΔBSF2RI.1 constructed in Example 6, and plasmid pΔBSF2RII.5 constructed in Example 7 were separately transfected to mouse COP cells (C. Tyndall et al., Nucleic Acid Res., 9, 6231, 1981) by the DEAE-dextran method (Secd, B. and Aruffo, A., PNAS, 84: 3365), and the cells were cultured in a DMEM medium containing 20% fetal calf serum (FCS). Using the same procedure as described in Example 1, it was determined whether the cultured cells expressed a desired protein, in a cell sorter using fluorescence staining (FACS440). The resulting results are shown in FIG. 7 (for pBSF2R.236), FIG. 8 (for pΔBSF2RI.1), and FIG. 9 (for pΔBSF2RII.5). As seen from these Figures, although COP cells transfected with pBSF2R.236 (FIG. 7B) and COP cells transfected with pBSF2RII.5 (FIG. 9B) were stained, COP cells transfected with pΔBSF2RI.1 (FIG. 8B) were not stained. The staining was prevented by the addition of an excess amount of recombinant BSI2 (FIG. 7C and FIG. 9C). As a result, it was confirmed that both the pBSF2R.236 and pBSF2RII.5 provide a protein having a BSF2 receptor activity, revealing that a protein wherein a protein of the amino acid sequence near the N-terminal of the native BSF2 receptor protein has been deleted, exhibits a BSF2 receptor activity.

Example 9

Figure 10A:
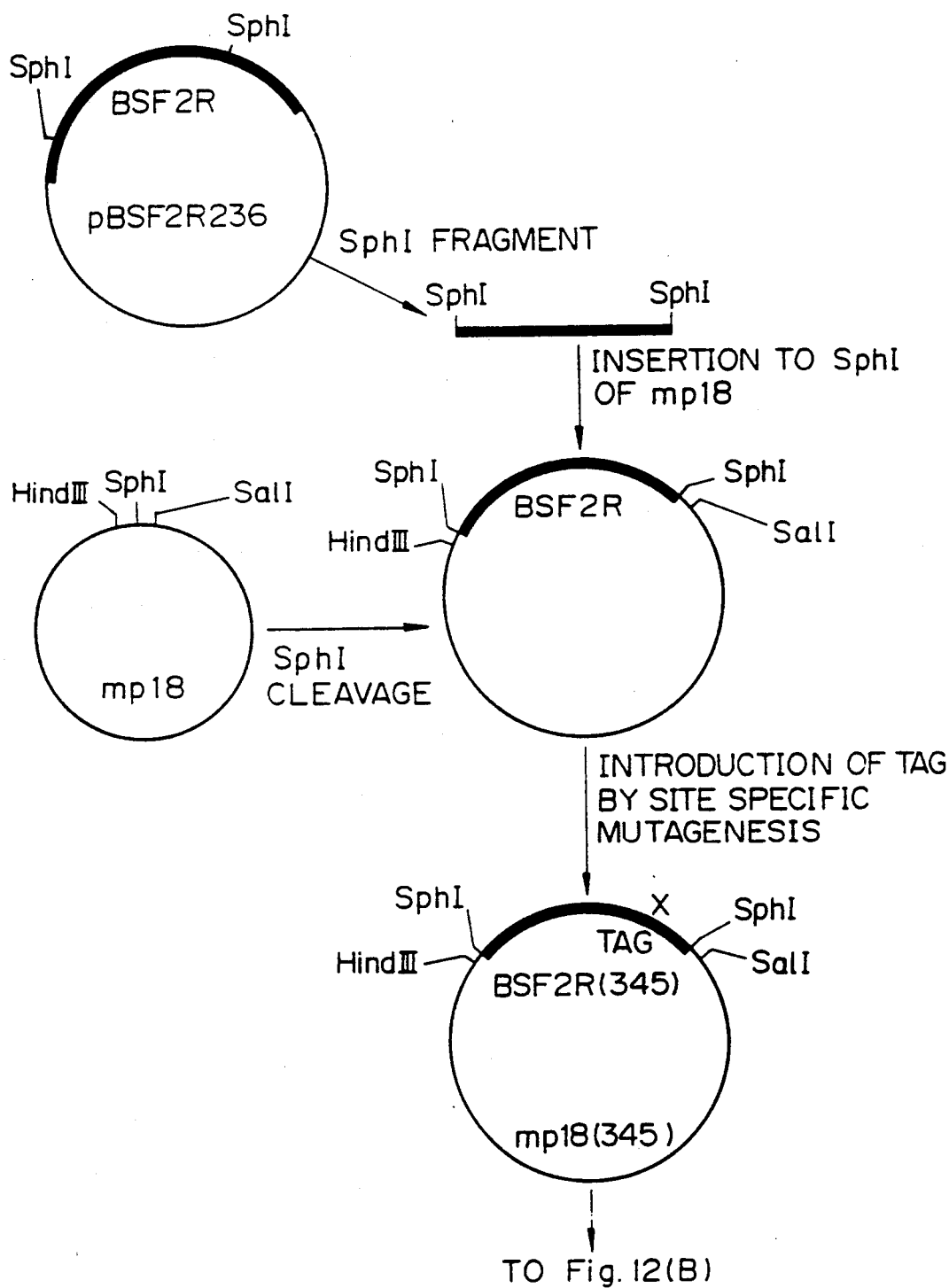
FIGS. 10A and B represent a process for the construction of plasmid phBABSF2R, and structure thereof.
Figure 10B:
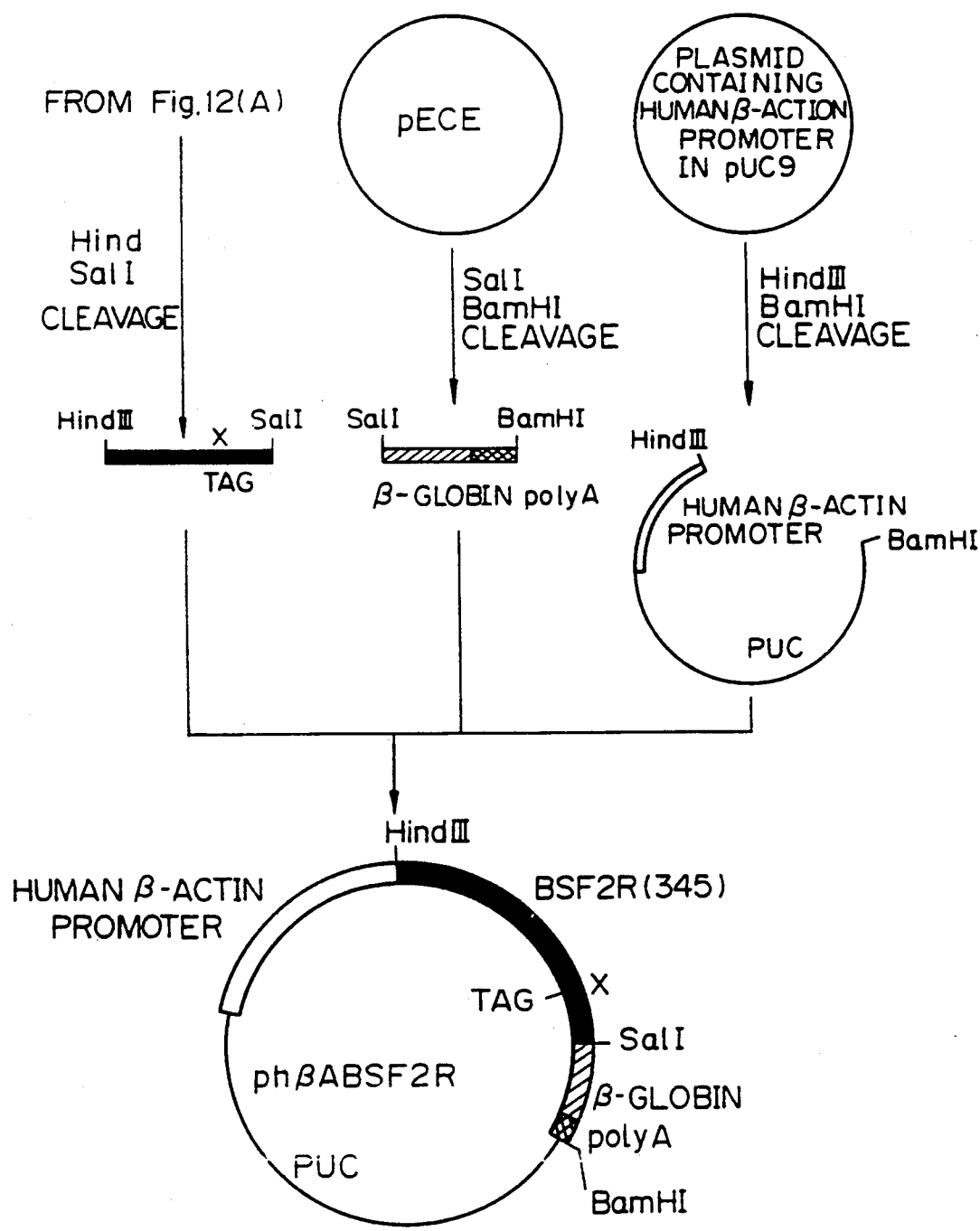
Figure 12:
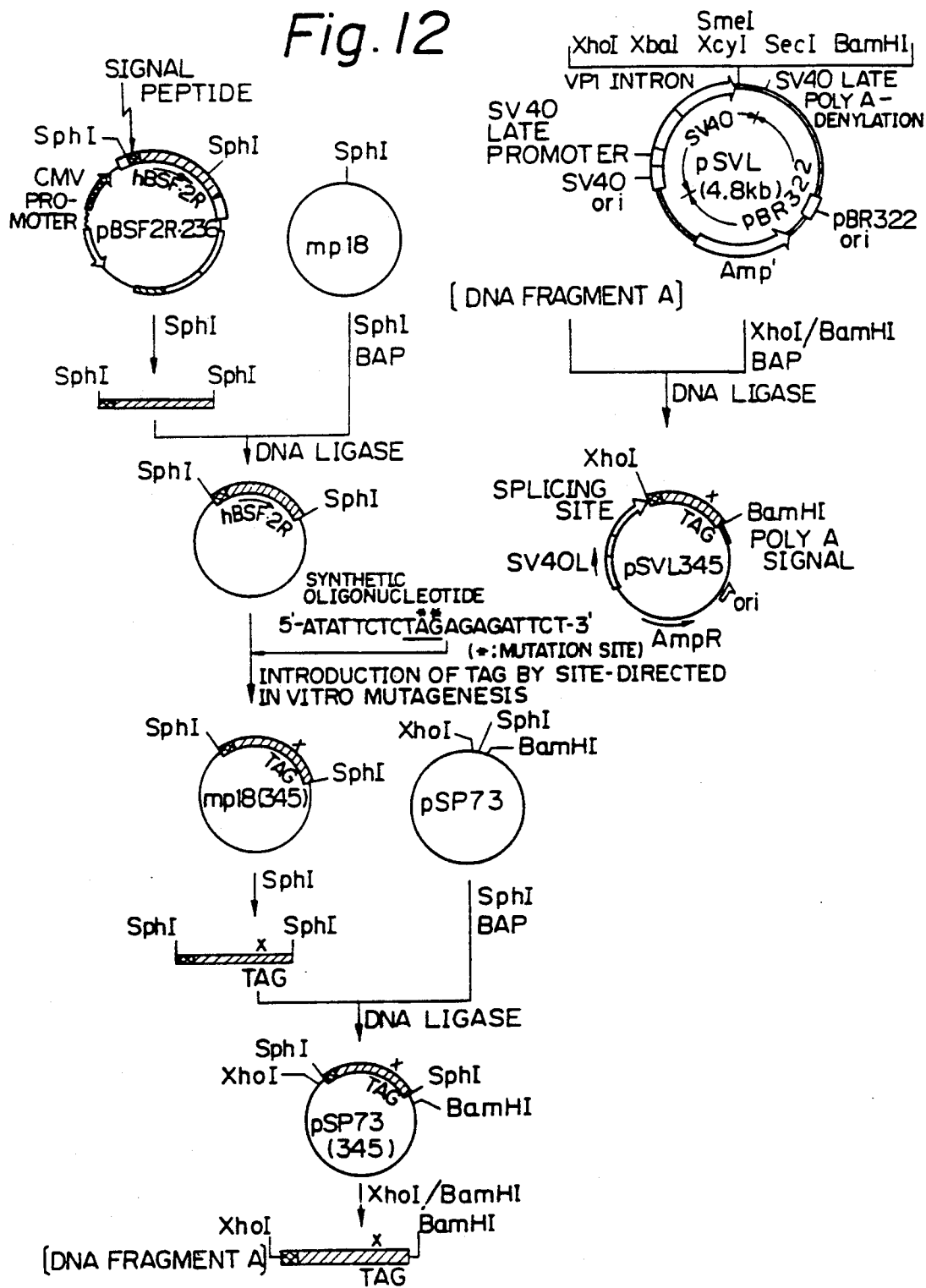
FIG. 12 represents a process for the construction of plasmid pSVL345.
Figure 13:
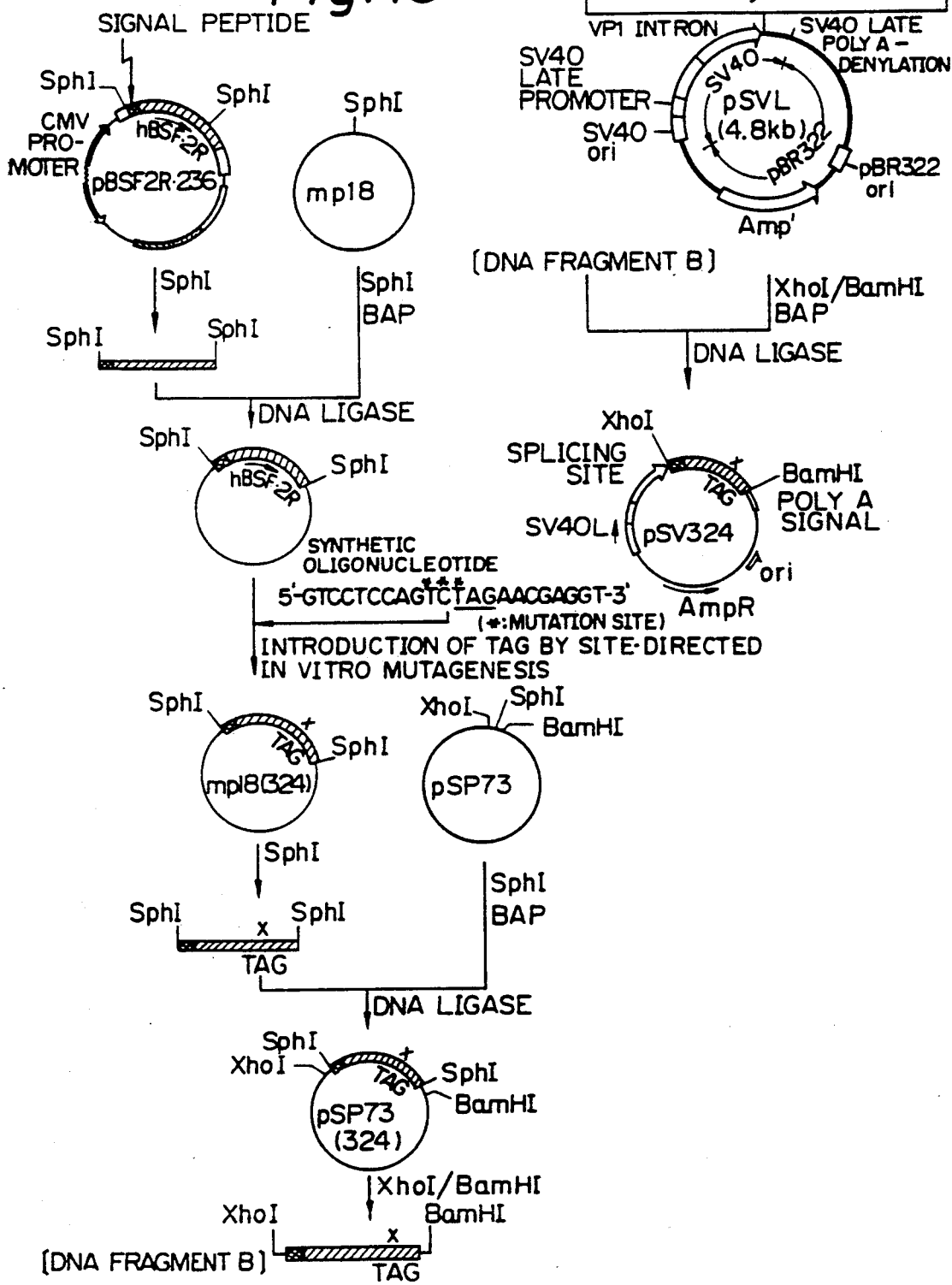
FIG. 13 represents a process for the construction of plasmid pSVL324.

Production of Soluble BSF2 Receptor Protein (1) (FIGS. 10 and 11)

To produce a soluble BSF2 receptor protein, a protein wherein a portion expected to be a membrane penetration region and a portion expected to be an intracellular protein region present at a C-terminal of the BSF2 receptor protein were deleted, was prepared. To this end, an expression plasmid phβABSF2R was constructed which comprised a vector portion based on plasmid PUC9; a BSF2 receptor expression unit comprising a human β actin promoter (S. Nakajima et al., Proc. Natl. Acad. Sci. USA, 82, 6133, 1985), a soluble BSF2 receptor cDNA, and a translation stop codon linked in this order.

Namely, the plasmid pBSF2R.236 was cleaved with Sphl to obtain a cDNA fragment containing codons for a first amino acid to a 402th amino acid of the native BSF2 receptor. This fragment was inserted to a phage vector M13 mp18 at the SphI site thereof, and site specific in-vitro mutagenesis was carried out using an oligonucleotide primer 5'-ATATTCT-CTAGAGAGATTCT-3' and a site specific in-vitro mutagenesis system (Amersham) to prepare a mutant phage M13 mp18 (345) wherein a TAG termination codon had been inserted immediately after the 344th amino acid codon. This mutant phage in a replicating form was cleaved with Hind III and SalI to obtain a DNA fragment (A) coding for an N-terminal side of the BSF2 receptor protein wherein a 345th amino acid codon had been replaced by a translation termination codon TAG. Moreover, a plasmid pECE (L. Ellis et al., Cell, 45, 721, 1986) containing β-globin poly A was cleaved with SalI and BamHI to obtain a DNA fragment (B) containing β-globin poly A. Further, a plasmid comprising a human β actin promoter inserted in a plasmid PUC9 was cleaved with HindIII and BamHI to obtain a linear plasmid (C) comprising a human β actin promoter and PUC9 vector. Next, these DNA fragments were ligated using DNA ligase to construct an expression plasmid phβABSF2R. A process for the construction of this plasmid and the structure thereof are shown in FIG. 10.

Soluble BSF2 receptor protein was prepared using the plasmid phβABSF2R, as follows. To mouse fibroblast cells (L cells, ATCC CCLl) cultured in a DMEM medium by a conventional procedure was added 20 μg/petri dish of phβABSF2R using a calcium phosphate method kit (Pharmacia). The medium was replaced the next day, and after a further culturing for two days, a culture supernatant was recovered. Detection of the soluble BSF2 receptor protein in the supernatant was carried out using an MT18 antibody prepared by the procedure described in Example 11 and $^{125}$I-BSF2 prepared by the procedure described in Example 1. Namely, 100 μl each of PBS containing 1 μg/ml of an MT18 antibody was put into each well of a 96-well microtiter plate, and the plate was incubated at 4° C. overnight. After washing, 100 μl/well of 1% BSA was added, and the plate was incubated for two hours at room temperature. After washing, 100 μl/well of the above-mentioned culture supernatant from the L medium was added, and the plate was incubated at a room temperature for two hours, and then washed. Next, 100 μl/well of $^{125}$I-BSF2, corresponding to 20,000 cpm/well, was added to the well, and the plate was incubated at room temperature for two hours, and then washed. The plate was cut to separate each well, and bound radioactivity was measured by a γ-counter. Further, to confirm the specificity of the product, the above-mentioned procedure was carried out using the supernatant supplemented with 200 ng/ml of non-labeled BSF2 instead of the supernatant alone.

For comparison, DMEM containing 10% FCS but not inoculated with cells, and a culture supernatant of L cells not transfected with plasmid were treated by the same procedure described above, and bound radioactivity was measured by a γ-counter.

The results are shown in FIG. 11. As seen from this Figure, in contrast with the DMEM medium containing 10% FCS and a culture supernatant of L cells not transfected with plasmid, a culture supernatant of L cells transfected with phβABSF2R contained a substance which binds to both the TM18 antibody and $^{125}$I-BSF2. Further, where a culture supernatant of L cells transfected with phβABSF2R and supplemented with 200 ng/ml non-labeled BSF2 was added instead of the supernatant alone, the bound radioactivity was significantly reduced. This shows that the product is a soluble BSF2 receptor.

Example 10

Production of Soluble BSF2 Receptor Protein (2) (FIGS. 12 to 18)

Construction of plasmid pSVL345

To produce a soluble BSF2 receptor protein in COS-1 cells, protein wherein a portion expected to be a membrane penetration region and a portion expected to be an intracellular protein region present at a C-terminal of the BSF2 receptor protein were deleted, was prepared. To this end, an expression plasmid pSVL345 was constructed which comprised a vector portion based on plasmid pSVL (Pharmacia); a BSF2 receptor expression unit comprising an SV40 late promoter contained in pSVL, a soluble BSF2 receptor cDNA, and a translation stop codon linked in this order; and SV40 polyadenylation signal.

Namely, the plasmid pBSF2R.236 was cleaved with SphI to obtain a cDNA fragment containing codons for a first amino acid to a 402th amino acid of the native BSF2 receptor. This fragment was inserted to a phage vector M13 mp18 at the SphI site thereof, and site specific in-vitro mutagenesis was carried out using an oligonucleotide primer 5'-ATATTCT-CTAGAGAGATTCT-3' and a site specific in-vitro mutagenesis system (Ameram) to prepare a mutant phage M13 mp18 (345) wherein a TAG termination codon had been inserted in place of the 345th amino acid codon. This mutant phage in a replicating form was cleaved with Hind III and SalI to obtain a DNA fragment coding for an N-terminal side of the BSF2 receptor protein wherein a 345th amino acid codon had been replaced by a translation termination codon TAG.

This DNA fragment was inserted in the SphI site of a plasmid pSP73 (available from Promegabiotch) to construct a plasmid wherein the DNA fragment has been inserted so that the XhoI site is present near to the 5'-side of BSF2 receptor and the BamHI site is present near to the 3'-side of the BSF2 receptor gene. This plasmid was cleaved with XhoI and BamHI to obtain a DNA fragment (A) containing a nucleotide sequence coding for 344 amino acids of the N-terminal side of a BSF2 receptor. On the other hand, the basic plasmid pSVL was cleaved with XhoI and BamHI, and treated with alkaline phosphatase to obtain a linearized plasmid DNA. Next, this linearized DNA and the DNA fragment (A) were ligated with T4 DNA ligase to construct an expression plasmid pSVL345. A process for the construction of this plasmid is set forth in FIG. 12.

Construction of Plasmid pSVL324

To produce a soluble BSF2 receptor protein, a protein wherein a portion expected to be a membrane penetration region and a portion expected to be an intracellular protein region present at a C-terminal of the BSF2 receptor protein were deleted, was prepared. To this end, an expression plasmid pSVL345 was constructed which comprised a vector portion based on plasmid pSVL (pharmacia); a BSF2 receptor expression unit comprising an SV40 late promoter contained in pSVL, a soluble BSF2 receptor cDNA, and a translation stop codon linked in this order; and SV40 polyadenylation signal.

Namely, the plasmid pBSF2R.236 was cleaved with SphI to obtain a cDNA fragment containing codons for a first amino acid to a 402th amino acid of the native BSF2 receptor. This fragment was inserted to a phage vector M13 mp18 at the SphI site thereof, and site specific in-vitro mutagenesis was carried out using an oligonucleotide primer 5,-GTCCTCCAGTCTAGAAC-GAGGT-3' and a site specific in-vitro mutagenesis system (Amersham) to prepare a mutant phage M13 mp18 (324) wherein a TAG termination codon had been inserted in place of the 324 amino acid codon. This mutant phage in a replicating form was cleaved with SphI to obtain a DNA fragment coding for an N-terminal side of the BSF2 receptor protein wherein a codon for 323th alanine has been changed to a codon for valine and a 324th amino acid codon had been replaced by a translation termination codon TAG.

This DNA fragment was inserted in the SphI site of a plasmid pSP73 (available from Promegabiotch) to construct a plasmid wherein the DNA fragment has been inserted so that the XhoI site is present near to the 5'-side of BSF2 receptor and the BamHI site is present near to the 3'-side of BSF2 receptor gene. This plasmid was cleaved with XhoI and BamHI to obtain a DNA fragment (B) containing a nucleotide sequence coding for 323 amino acids of the N-terminal side of a BSF2 receptor. On the other hand, the basic plasmid pSVL was cleaved with XhoI and BamHI, and treated with alkaline phosphatase to obtain a linearized plasmid DNA. Next, this linearized DNA nd the DNA fragment (B) were ligated with T4 DNA ligase to construct an expression plasmid pSVL324. A process for the construction of this plasmid is set forth in FIG. 13.

Expression of Soluble BSF2 Receptor Protein

An expression of a soluble BSF2 receptor protein using the above-mentioned plasmids pSVL345 and pSVL324 was carried out as follow. COS-1 cells (ATCC CRL 1650) derived from kidney cells of an African green monkey were cultured in DMEM supplemented with 10%(v/v) fetal calf serum (Gibco), by a conventional procedure. To the cultured cells, the plasmids pSVL345 and pSVL324, and plasmid pSVL (Moch) not containing the BSF2 expression unit, were separately transfected by a calcium phosphate method (Wigler et al. Cell, 14, 725–731, 1978). Namely, for each palsmid, $\times 10^6$ cells/10 ml was put into a petri disk having a diameter of 100 mm, and cultured overnight, and 20 µg of plasmid in 1 ml of calcium phosphate solution (Chu, G. and Sharp, P. A., Gene, 13, 197–202, 1981) was added to each culture. the next day, the medium was exchanged and 10 ml of the medium was added, and after a further culturing for three days, a supernatant was recovered.

Detection of Soluble BSF2 Receptor in Supernatant

First, an enzyme immunoassay was carried out using an MT18 antibody described in Example 11. Namely, the supernatant prepared as described above was diluted, and 200 µl of the diluted supernatant was put into each well of 96-well microtiter plate. After incubation at 4° C. overnight, the plate was washed with a washing solution. Next, 1% of a BSA solution was added to each well, and the plate was allowed to stand at a room temperature for 90 minutes, to block the wells. Next, the plate was washed, and the MT18 antibody was added to the wells and incubation was carried out at a room temperature for 90 minutes. Again the plate was washed, and an antimouse IgG26 rabbit antibody was added to the wells, and incubation was carried out at a room temperature for 60 minutes, then after washing the plate, an enzyme-labeled anti-rabbit IgG goat antibody was added to the wells, an incubation was carried out at a room temperature for 60 minutes. After again washing the plate, p-nitrophenyl phosphate as a substrate was added to the wells to carry out an enzyme reaction for 30 minutes, and after the reaction, the absorbance (O.D. 405-600 nm) was measured by a microplate reader (Toso, Japan).

Figure 14:
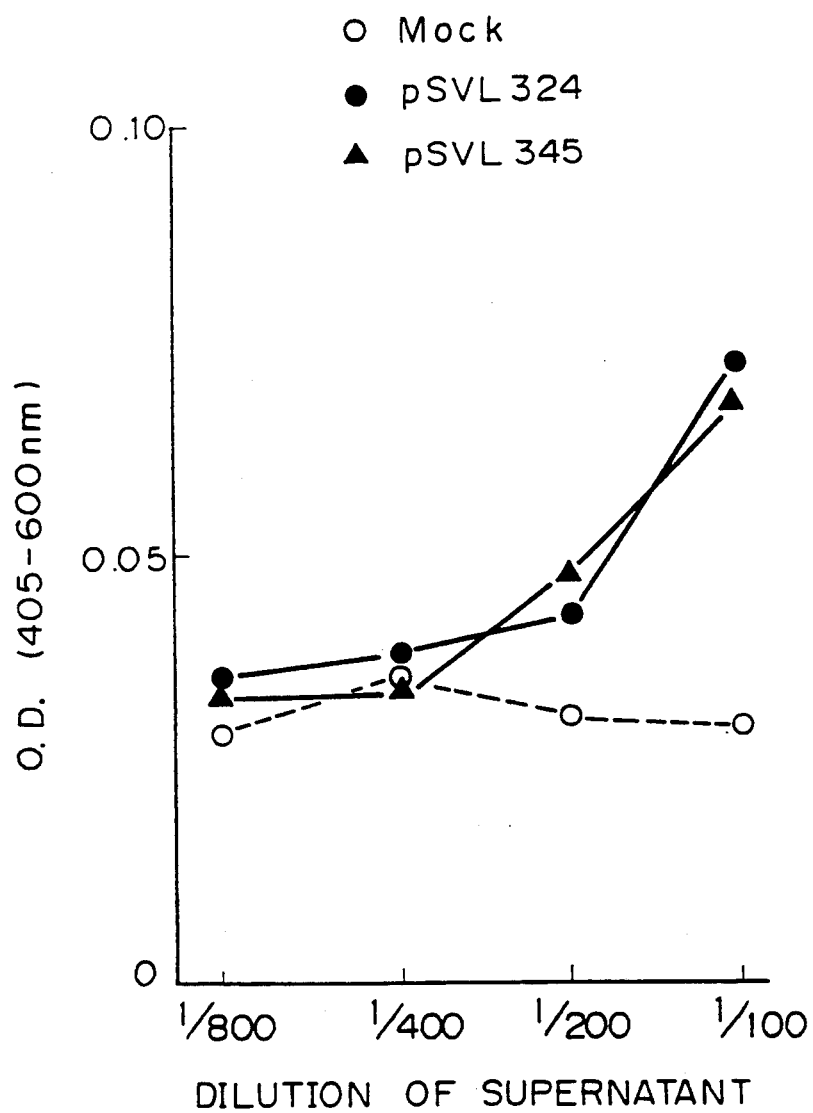
FIG. 14 shows a result of the detection by enzyme immuno assay of a soluble BSF2 receptor protein in a supernatant from a culture of COS-1 cells transfected with plasmid pSVL345 or pSVL324.
Figure 15:
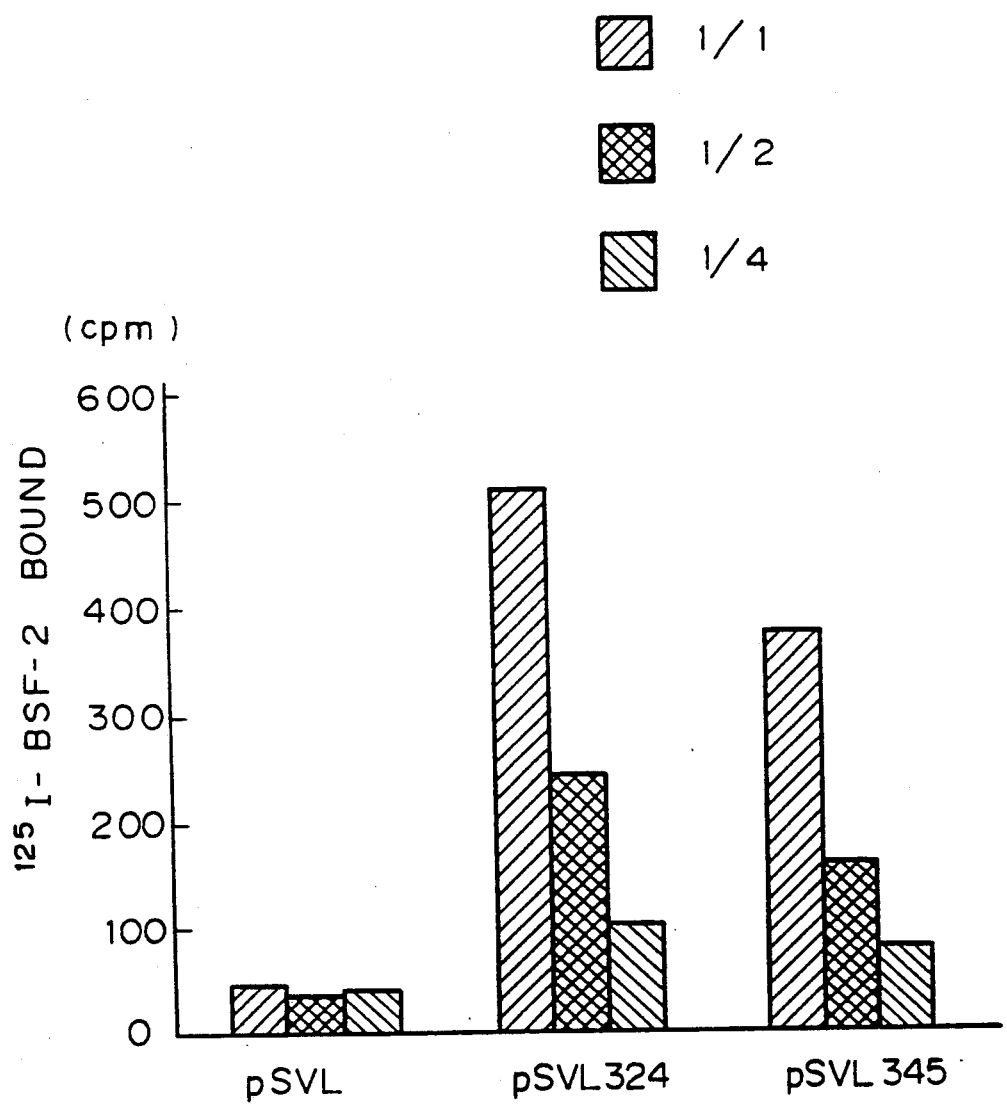
FIG. 15 is a graph showing a specific binding to BSF2 of products in a supernatant from a culture of COS-1 cells transfected with plasmid pSVL345 or pSVL324.
Figure 16:
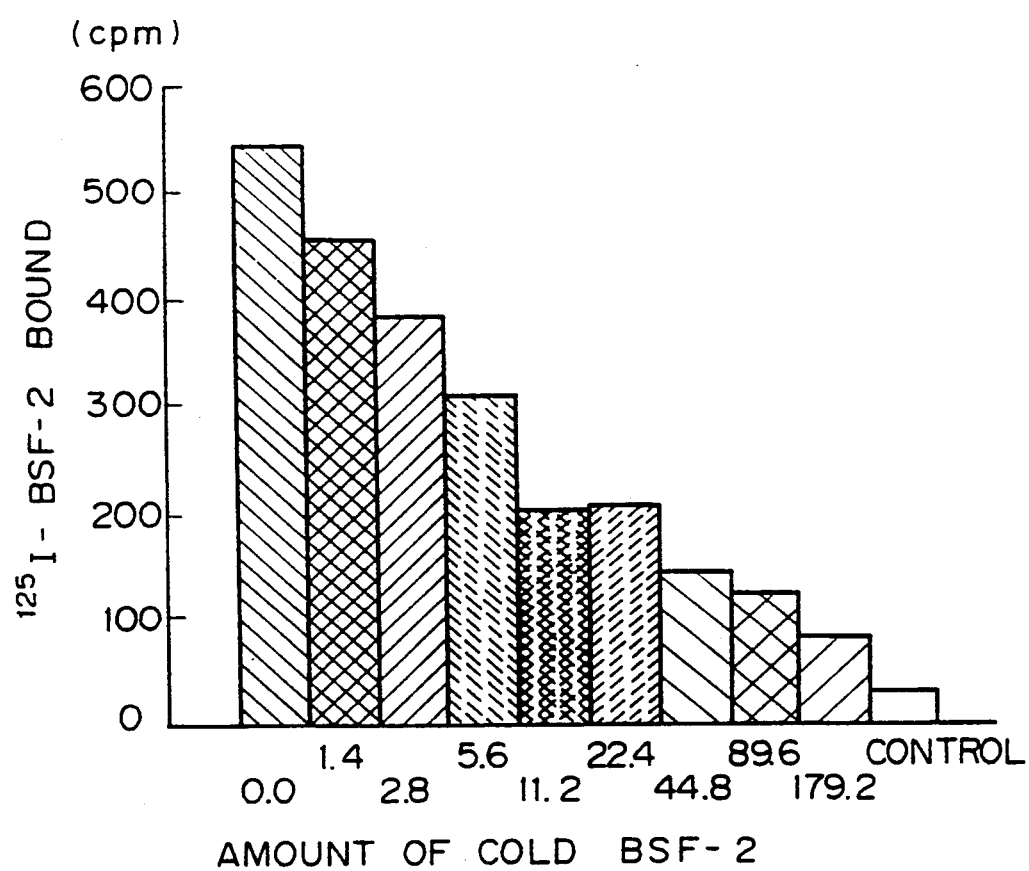
FIG. 16 is a graph showing a competitive inhibition of cold BSF-2 and $^{125}$I-BSF2 for the binding to product in a supernatant from a culture of COS-1 cells transfected with plasmic SVL345 or pSVL324.
Figure 17:
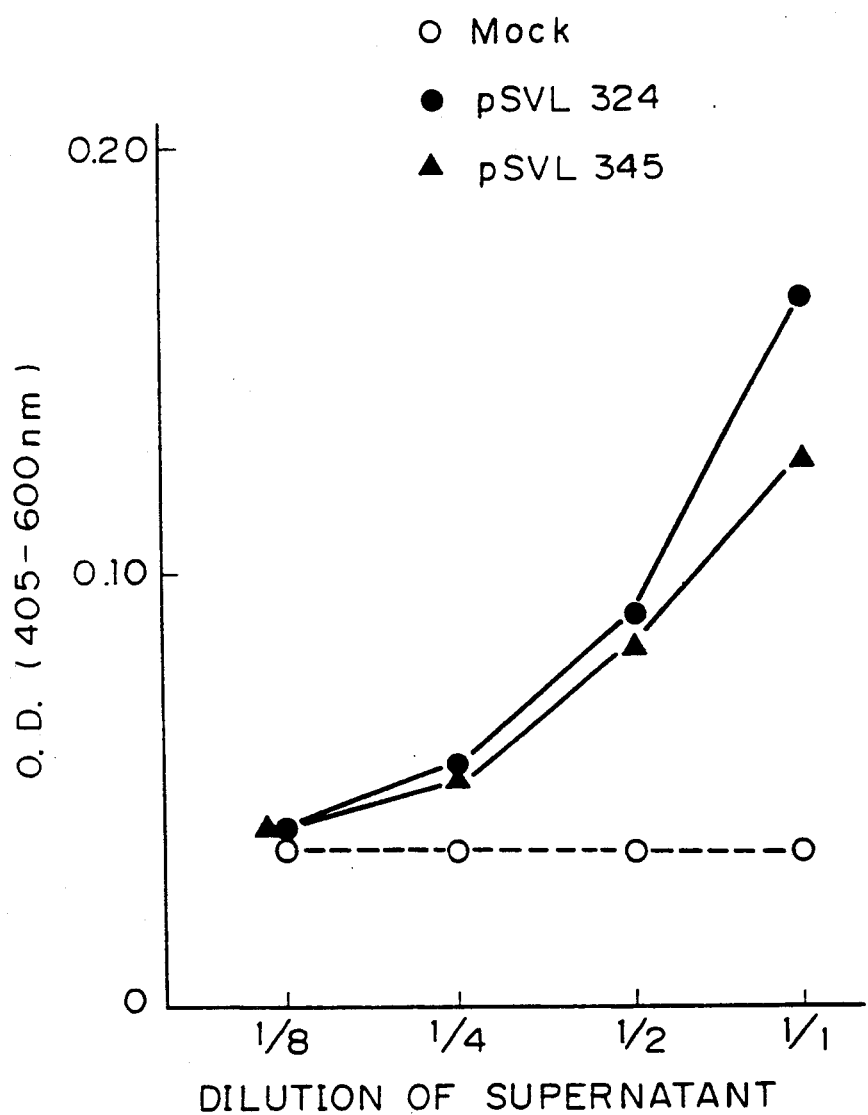
FIG. 17 is a graph showing that product in a supernatant from a culture of COS-1 cells transfected with plasmid pSVL345 or pSVL324 binds to both the MT18 antibody and BSF2.
Figure 18:
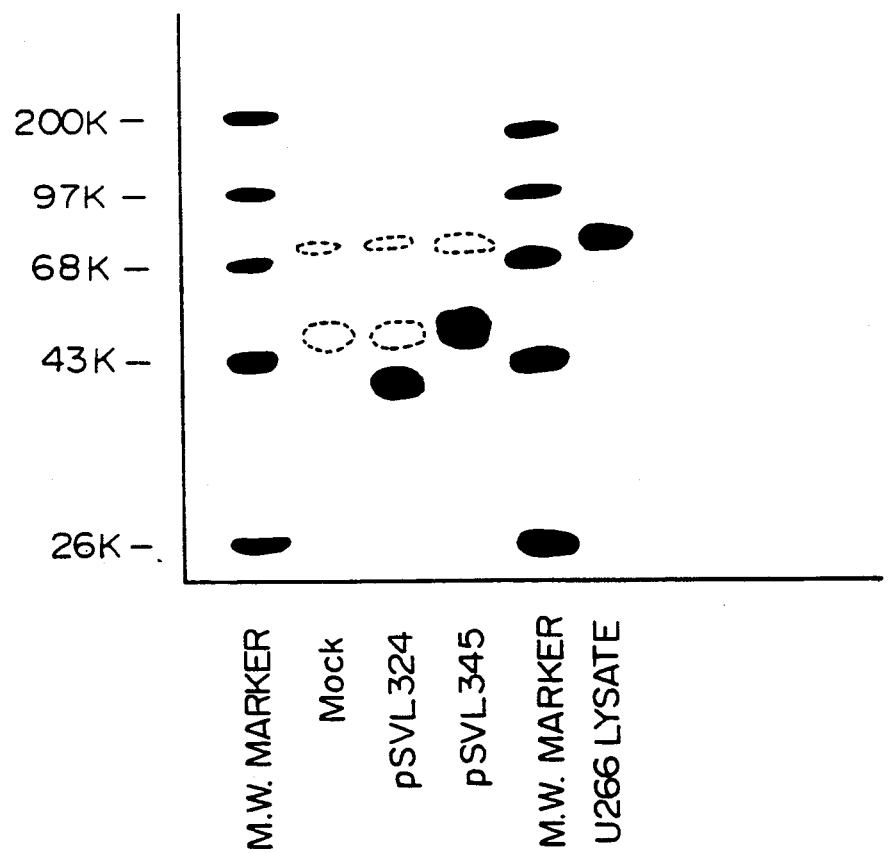
FIG. 18 represents an electrophoresis pattern wherein the product in a supernatant from a culture of COS-1 cells transfected with plasmid pSVL345 or pSVL324 and a lysate of BSF2 receptor-producer U266 cells as a control were separated by SDS-PAGE and detected with an MT18 antibody.

The result is set forth in FIG. 14. As seen from the FIG. 14, supernatants from COS-1 cells transfected with pSVL345 and pSVL324, respectively, contained a product which binds to the MT18 antibody, but a supernatant from COS-1 cells transfected with pSVL not containing the BSF2 receptor expression unit did not contain a product which binds to the MT18 antibody.

Next, a soluble BSF2 receptor in the supernatants was detected by a method using the MT18 antibody and $^{125}I$-BSF2, by the same procedure as in Example 9. The result is set forth in FIG. 15. As seen from the FIG. 15, in comparison to the supernatant from COS-1 cells transfected with pSVL, the supernatants from COS-1 cells transfected with pSVL345 and pSVL324, respectively, contained a product which binds to both the MT18 antibody and $^{125}I$-BSF2. Moreover, where cold BSF2 was added to the supernatant, the count was dose-dependently decreased. This confirms that the product in the supernatant was a soluble BSF2 receptor (see FIG. 16).

As another confirmation, the presence of a soluble BSF2 receptor in the supernatant was confirmed by a method using the MT18 antibody, BSF2, and an anti-BSF2 rabbit antibody. Namely, 200 μl of 5 μg/ml MT18 antibody was added to each well of a microtiter plate, and the plate was incubated at 40° C. overnight. After washing the plate, the wells were blocked with 1% of a BSA solution at a room temperature for 90 minutes, and after again washing the plate, a suitably diluted culture supernatant was added to the well, and an incubation was carried out at a room temperature for 60 minutes. Then, after washing, a 100 ng/ml BSF2 solution containing 10% FCS was added to the well, which was incubated at a room temperature for 60 minutes. Again after washing, 500 ng/ml anti-BSF2 rabbit IgG antibody was added to the well, and incubation was carried out at a room temperature for 60 minutes, and after another washing, an enzyme-labeled anti-rabbit IgG goat IgG antibody was added to the well and incubation was carried out at a room temperature for 60 minutes. Subsequently, the plate was treated by the same procedure as described above. The result is set forth in FIG. 17. In comparison with a supernatant from COS-1 cells transfected with pSVL, it was confirmed that supernatants from COS-1 cells transfected with pSVL345 and PSVL324, respectively, contained a product which binds to both the MT18 antibody and BSF2.

Finally, the supernatants were subjected to SDS-polyacrylamide gel electrophoresis, the electrophoresis pattern was transblotted to a nitrocellulose sheet, and the MT18 antibody was added to the microcellulose sheet. Next, to the nitrocellulose sheet was added a biotinated anti-mouse IgG antibody followed by streptoavidinalkaline phosphatase. Finally, NBT/BCIP as a substrate was added to the nitrocellulose sheet to develop the products. The result is set forth in FIG. 18. Supernatant from COS-1 cells transfected with pSVL324 exhibited a band at 42kD, and supernatant from COS-1 cells transfected with pSVL345 exhibited a band at 50 kD, revealing the presence of a soluble BSF2 receptor in the supernatants.

Figure 19:
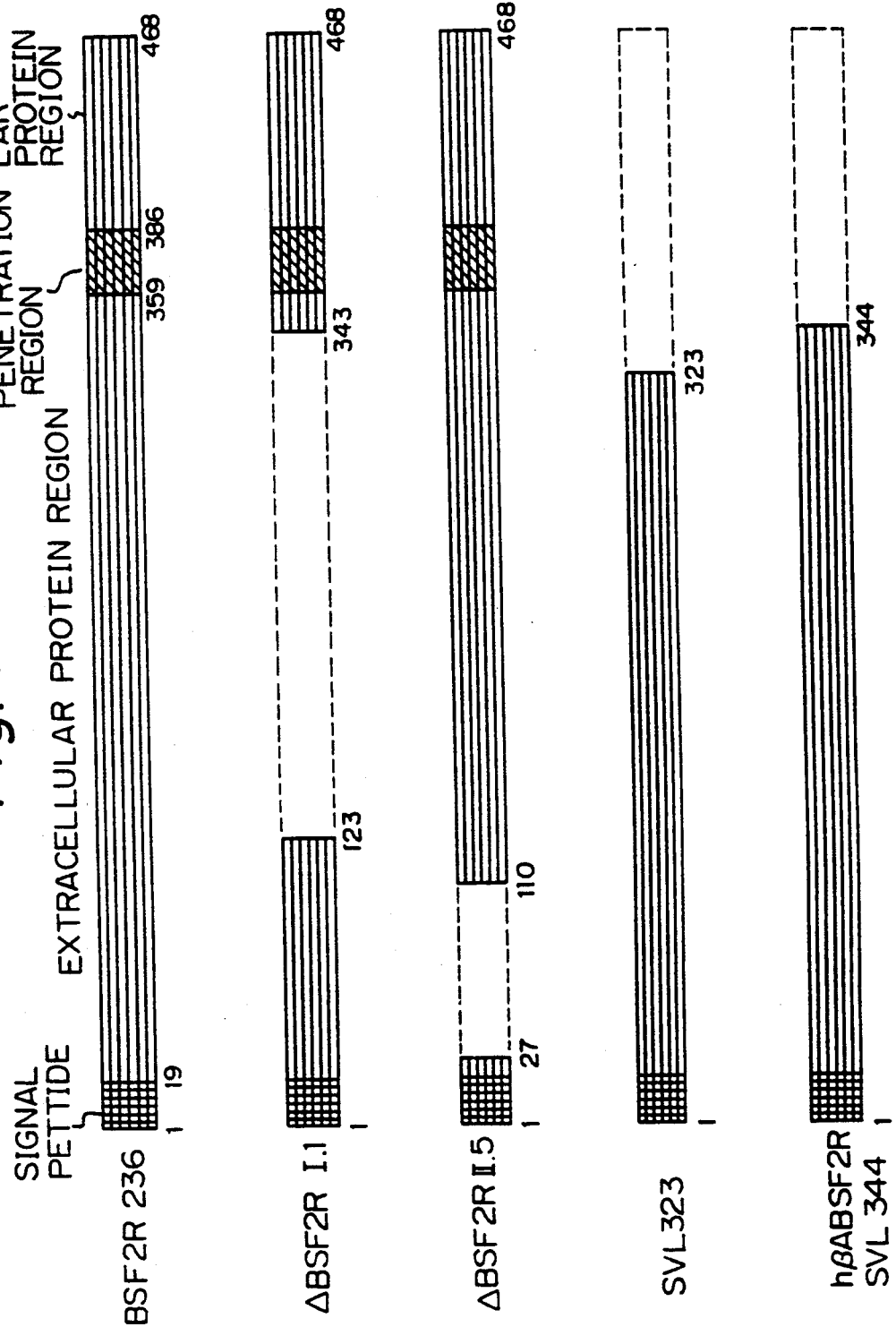
FIG. 19 schematically represents structures of the BSF2 receptor protein and shortened analogues thereof.

FIG. 19 represents the structures of proteins produced in Examples 8, 9, and 10. In this figure, BSF2R.236 is a protein produced by a plasmid pBSF2R.236, and corresponds to a native BSF2 receptor. ΔBSF2RI.1 represents a protein produced by a plasmid pΔBSF2RI.1, ΔBSF2RII.5 represents a protein produced by a plasmid pΔBSF2RII.5, SVL324 represents a protein produced by a plasmid pSVL324, hβABSF2R represents a protein produced by a plasmid phβABSF2R and SVL345 represents a protein produced by plasmid pSVL345. Since not only BSF2R.236, but also ΔBSF2RII.5, DRN1, and hβABSF2R exhibit a BSFR receptor activity, it was confirmed that shortened proteins wherein a portion of the amino acid sequence near the N-terminal of the native BSF2 receptor protein has been deleted, and shortened proteins wherein a portion of C-terminal including a membrane penetration region and an intracellular protein region of the native BSF2 receptor protein has been deleted, still exhibit a BSF2 receptor activity.

Example 11

Production of Monoclonal Antibody to BSF2 Receptor

To prepare an immunogen for the production of a monoclonal antibody to the BSF2 receptor, a mouse T cell line expressing human BSF2 receptor on the surface was prepared as follows. The plasmid pBSF2R.236 described in Example 4 and the plasmid pSV2 neo were cotransfected to cells of a mouse cell line CTLL-2 (ATCC TIB214), then subjected to a screening procedure using G-418, and eventually a cell line expressing about 30,000/cell of BSF2 receptor was established, and designated as CTBC3.

Figure 20A:
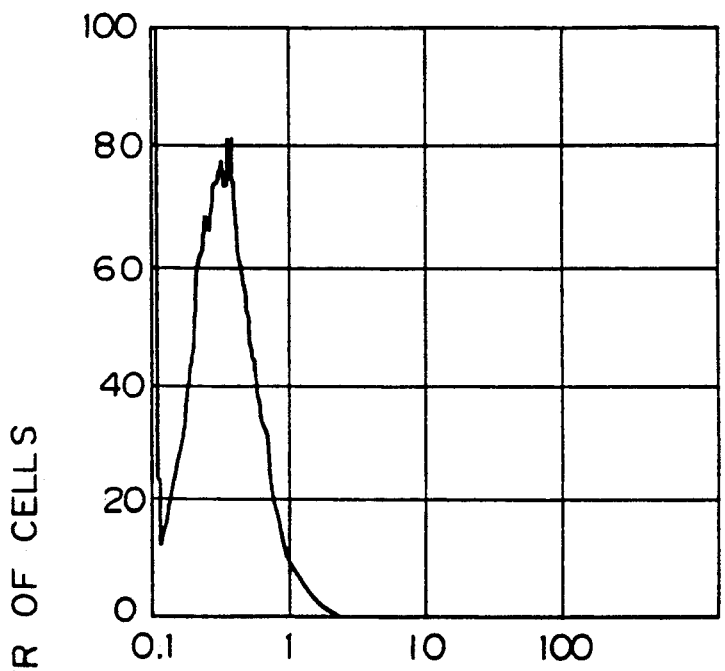
FIG. 20 is a graph showing fluorescence intensity versus cell frequency, showing that the MT18 antibody binds only to cells producing the BSF2 receptor. Wherein A represents a result for JURKAT cells which do not produce the BSF2 receptor, and B represents a result for NJBC8 cells which produce the BSF2 receptor.
Figure 20B:
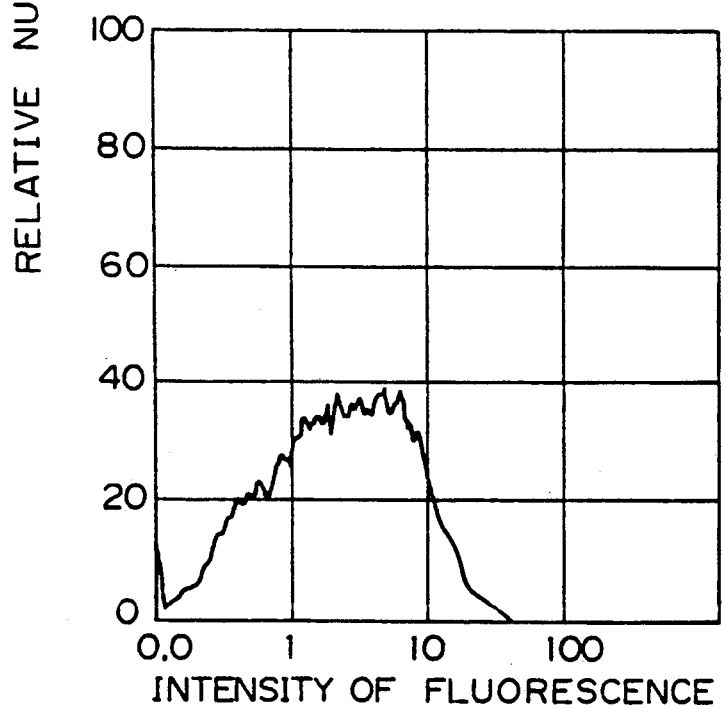

The CTBC3 cells were cultured in RPMI 1640 by a conventional procedure, and the cultured cells were washed three times with PBS buffer. The washed cells were intraperitonealy injected to C57BL6 mouse in an amount of $1 \times 10^7$ cells/mouse, once a week for a total of six times, to immunize the mouse. Spleen cells from the immunized mouse were fused with a myeloma cell line P301 by a conventional procedure using polyethyleneglycol, and a desired hybridoma was selected as follows. A human T cell line JURKAT (ATCC CRL8163), which is BSF2 receptor negative, was cotransfected with pBSF2R.236 and pSV2 neo, and the transfected cells were screened. A cell line, which expresses 100,000/cell of BSF2 receptor, was established and designated as NJBC8. One clone of hybridoma, which recognizes NJBC8 cells lyzed with NP40 and does not recognize JURKAT cells lyzed with NP40, was isolated and designated as MT18. An monoclonal antibody produced by the hybridoma MT18 is designated as an MT18 antibody. FIG. 20 shows that the MT18 antibody specifically recognizes the BSF2 receptor. In this figure, A represents a graph of fluorescence intensity versus cell frequency where JURKAT cells were stained by an MT18 antibody labeled with fluoresceinisocyanate, and B represents a similar result where NJBC8 cells were similarly stained.

I claim:

1. An isolated receptor protein consisting essentially of an active site for binding human B cell stimulating factor-2, wherein said active site is located between amino acid 123 and amino acid 323 in amino acid sequence (I):

(N-terminal)  (I)
Met Leu Ala Val Gly Cys Ala Leu Leu Ala Ala
Leu Leu Ala Ala Pro Gly Ala Ala Leu Ala Pro
Arg Arg Cys Pro Ala Gln Glu Val Ala Arg Gly
Val Leu Thr Ser Leu Pro Gly Asp Ser Val Thr
Leu Thr Cys Pro Gly Val Glu Pro Glu Asp Asn
Ala Thr Val His Trp Val Leu Arg Lys Pro Ala
Ala Gly Ser His Pro Ser Arg Trp Ala Gly Met
Gly Arg Arg Leu Leu Leu Arg Ser Val Gln Leu
His Asp Ser Gly Asn Tyr Ser Cys Tyr Arg Ala
Gly Arg Pro Ala Gly Thr Val His Leu Leu Val
Asp Val Pro Pro Glu Pro Gln Leu Ser Cys
Phe Arg Lys Ser Pro Leu Ser Asn Val Val Cys
Glu Trp Gly Pro Arg Ser Thr Pro Ser Leu Thr
Thr Lys Ala Val Leu Leu Val Arg Lys Phe Gln
Asn Ser Pro Ala Glu Asp Phe Gln Glu Pro Cys
Gln Tyr Ser Gln Glu Ser Gln Lys Phe Ser Cys
Gln Leu Ala Val Pro Glu Gly Asp Ser Ser Phe
Tyr Ile Val Ser Met Cys Val Ala Ser Ser Val
Gly Ser Lys Phe Ser Lys Thr Gln Thr Phe Gln
Gly Cys Gly Ile Leu Gln Pro Asp Pro Pro Ala
Asn Ile Thr Val Thr Ala Val Ala Arg Asn Pro
Arg Trp Leu Ser Val Thr Trp Gln Asp Pro His
Ser Trp Asn Ser Ser Phe Tyr Arg Leu Arg Phe
Glu Leu Arg Tyr Arg Ala Glu Arg Ser Lys Thr
Phe Thr Thr Trp Met Val Lys Asp Leu Gln His
His Cys Val Ile His Asp Ala Trp Ser Gly Leu
Arg His Val Val Gln Leu Arg Ala Gln Glu Glu
Phe Gly Gln Gly Glu Trp Ser Glu Trp Ser Pro
Glu Ala Met Gly Thr Pro Trp Thr Glu Ser Arg
Ser Pro Pro Ala Glu Asn Glu Val Ser Thr Pro
Met Gln Ala Leu Thr Thr Asn Lys Asp Asp Asp
Asn Ile Leu Phe Arg Asp Ser Ala Asn Ala Thr
Ser Leu Pro Val Gln Asp Ser Ser Ser Val Pro
Leu Pro Thr Phe Leu Val Ala Gly Gly Ser Leu
Ala Phe Gly Thr Leu Leu Cys Ile Ala Ile Val
Leu Arg Phe Lys Lys Thr Trp Lys Leu Arg Ala
Leu Lys Glu Gly Lys Thr Ser Met His Pro Pro
Tyr Ser Leu Gly Gln Leu Val Pro Glu Arg Pro
Arg Pro Thr Pro Val Leu Val Pro Leu Ile Ser
Pro Pro Val Ser Pro Ser Ser Leu Gly Ser Asp
Asn Thr Ser Ser His Asn Arg Pro Asp Ala Arg
Asp Pro Arg Ser Pro Tyr Asp Ile Ser Asn Thr -continued
Asp Tyr Phe Phe Pro Arg.
  (C-terminal).

2. The isolated receptor protein according to claim 1, wherein said receptor protein contains an amino acid sequence consisting essentially of amino acids 1 to 27 fused to amino acids 110 to 468 in amino acid sequence (I).

3. The isolated receptor protein according to claim 1, wherein said receptor protein contains an amino acid sequence consisting essentially of amino acids 1 to 323 in amino acid sequence (I).

4. The isolated receptor protein according to claim 1, wherein said receptor protein contains an amino acid sequence consisting essentially of amino acids 1 to 344 in said amino acid sequence (I).

5. The isolated receptor protein according to claim 1, wherein said receptor protein is a fusion protein.

6. The isolated receptor protein according to claim 1, wherein said receptor protein consists essentially of the following amino acid sequence:

Arg Lys Ser Pro Leu Ser Asn Val Val Cys
Glu Trp Gly Pro Arg Ser Thr Pro Ser Leu Thr
Thr Lys Ala Val Leu Leu Val Arg Lys Phe Gln
Asn Ser Pro Ala Glu Asp Phe Gln Glu Pro Cys
Gln Tyr Ser Gln Glu Ser Gln Lys Phe Ser Cys
Gln Leu Ala Val Pro Glu Gly Asp Ser Ser Phe
Tyr Ile Val Ser Met Cys Val Ala Ser Ser Val
Gly Ser Lys Phe Ser Lys Thr Gln Thr Phe Gln
Gly Cys Gly Ile Leu Gln Pro Asp Pro Pro Ala
Asn Ile Thr Val Thr Ala Val Ala Arg Asn Pro
Arg Trp Leu Ser Val Thr Trp Gln Asp Pro His
Ser Trp Asn Ser Ser Phe Tyr Arg Leu Arg Phe
Glu Leu Arg Tyr Arg Ala Glu Arg Ser Lys Thr
Phe Thr Thr Trp Met Val Lys Asp Leu Gln His
His Cys Val Ile His Asp Ala Trp Ser Gly Leu
Arg His Val Val Gln Leu Arg Ala Gln Glu Glu
Phe Gly Gln Gly Glu Trp Ser Glu Trp Ser Pro
Glu Ala Met Gly Thr Pro Trp Thr Glu Ser Arg
Ser Pro Pro Ala.

* * * * *

UNITED STATES PATENT AND TRADEMARK OFFICE
CERTIFICATE OF CORRECTION

PATENT NO. : 5,171,840
DATED : December 15, 1992
INVENTOR(S) : Tadamitsu Kishimoto It is certified that error appears in the above-indentified patent and that said Letters Patent is hereby corrected as shown below:

The title page, should read -- 7 Claims, 25 Drawing Sheets --.

Column 22, please add claim 7, as follows:

7. An isolated receptor protein according to claim 1, wherein said receptor protein consists of amino acids 1 to 468 in amino acid sequence (I).

Signed and Sealed this

Thirtieth Day of November, 1993

Attest:

BRUCE LEHMAN

*Attesting Officer*      *Commissioner of Patents and Trademarks*